(12) United States Patent
Reisinger

(10) Patent No.: US 9,306,318 B2
(45) Date of Patent: Apr. 5, 2016

(54) CERAMIC BUSHING WITH FILTER

(75) Inventor: Andreas Reisinger, Alzenau (DE)

(73) Assignee: Heraeus Deutschland GmbH & Co. KG, Hanau (DE)

( * ) Notice: Subject to any disclaimer, the term of this patent is extended or adjusted under 35 U.S.C. 154(b) by 158 days.

(21) Appl. No.: 13/361,374

(22) Filed: Jan. 30, 2012

(65) Prior Publication Data

US 2012/0197368 A1 Aug. 2, 2012

Related U.S. Application Data

(60) Provisional application No. 61/438,042, filed on Jan. 31, 2011.

(30) Foreign Application Priority Data

Jan. 31, 2011 (DE) .......................... 10 2011 009 859

(51) Int. Cl.
*A61N 1/05* (2006.01)
*C04B 35/64* (2006.01)
*H01R 13/52* (2006.01)
*A61N 1/375* (2006.01)
(Continued)

(52) U.S. Cl.
CPC .......... *H01R 13/5224* (2013.01); *A61N 1/3754* (2013.01); *H01R 13/719* (2013.01); *H01G 4/35* (2013.01); *H01R 13/6466* (2013.01); *H01R 2201/12* (2013.01); *H03H 2001/0042* (2013.01)

(58) Field of Classification Search
CPC ............................... A61N 1/3754; H01G 4/35
USPC ............................ 174/659; 607/116; 264/614
See application file for complete search history.

(56) References Cited

U.S. PATENT DOCUMENTS 3,025,441 A * 3/1962 West ........................ H01B 1/02
205/172
3,063,144 A 11/1962 Palmour, III
(Continued)

FOREIGN PATENT DOCUMENTS

DE 69729719 7/2005
DE 102006054249 5/2008
(Continued)

OTHER PUBLICATIONS

The Restriction Requirement for U.S. Appl. No. 13/361,322 mailed Nov. 14, 2013 (7 pages).
(Continued)

*Primary Examiner* — William H Mayo, III
*Assistant Examiner* — Hiram E Gonzalez
(74) *Attorney, Agent, or Firm* — Dicke, Billig & Czaja, PLLC

(57) ABSTRACT

One aspect relates to an electrical bushing for use in a housing of an implantable medical device. The electrical bushing includes at least one electrically insulating base body and at least one electrical conducting element. The conducting element is set up to establish, through the base body, at least one electrically conductive connection between an internal space of the housing and an external space. The conducting element is hermetically sealed with respect to the base body. The at least one conducting element includes at least one cermet. The electrical bushing includes an electrical filter structure. The at least one conducting element forms at least one electrically conducting surface of the filter structure.

15 Claims, 3 Drawing Sheets

(51) Int. Cl.
*H01R 13/719* (2011.01)
*H01G 4/35* (2006.01)
*H01R 13/6466* (2011.01)
*H03H 1/00* (2006.01)

(56) References Cited

U.S. PATENT DOCUMENTS

| | | | |
|---|---|---|---|
| 3,646,405 A | 2/1972 | Wallis et al. | |
| 3,979,187 A | 9/1976 | Scherer | |
| 4,152,540 A | 5/1979 | Duncan et al. | |
| 4,159,075 A | 6/1979 | Ljung et al. | |
| 4,217,137 A | 8/1980 | Kraska et al. | |
| 4,225,262 A | 9/1980 | Koop et al. | |
| 4,315,054 A | 2/1982 | Sack et al. | |
| 4,354,964 A | 10/1982 | Hing et al. | |
| 4,488,673 A | 12/1984 | Hopper, Jr. | |
| 4,602,956 A | 7/1986 | Partlow et al. | |
| 4,678,868 A | 7/1987 | Kraska et al. | |
| 4,991,582 A | 2/1991 | Byers et al. | |
| 5,043,535 A | 8/1991 | Lin | |
| 5,515,604 A | 5/1996 | Horine et al. | |
| 5,735,884 A | 4/1998 | Thompson et al. | |
| 5,738,270 A | 4/1998 | Malmgren | |
| 5,769,874 A | 6/1998 | Dahlberg | |
| 5,796,019 A | 8/1998 | Lupton et al. | |
| 5,861,714 A | 1/1999 | Wei et al. | |
| 5,870,272 A | 2/1999 | Seifried et al. | |
| 6,093,476 A | 7/2000 | Horiuchi et al. | |
| 6,414,835 B1 | 7/2002 | Wolf et al. | |
| 6,643,903 B2 | 11/2003 | Stevenson et al. | |
| 6,660,116 B2 | 12/2003 | Wolf et al. | |
| 6,841,731 B1 | 1/2005 | Zanello | |
| 6,999,818 B2 | 2/2006 | Stevenson et al. | |
| 7,035,076 B1 | 4/2006 | Stevenson | |
| 7,038,900 B2 | 5/2006 | Stevenson et al. | |
| 7,136,273 B2 | 11/2006 | Stevenson et al. | |
| 7,145,076 B2 | 12/2006 | Knappen et al. | |
| 7,174,219 B2 | 2/2007 | Wahlstrand et al. | |
| 7,174,223 B2 | 2/2007 | Dalton et al. | |
| 7,260,434 B1 | 8/2007 | Lim et al. | |
| 7,274,963 B2 | 9/2007 | Spadgenske | |
| 7,341,802 B1 | 3/2008 | Ota et al. | |
| 7,437,817 B2 | 10/2008 | Zhang et al. | |
| 7,480,988 B2 | 1/2009 | Ok et al. | |
| 7,502,217 B2 | 3/2009 | Zhao et al. | |
| 7,561,917 B2 | 7/2009 | Wegrzyn, III et al. | |
| 7,564,674 B2 | 7/2009 | Frysz et al. | |
| 7,630,768 B1 | 12/2009 | Coffed et al. | |
| 7,706,124 B2 | 4/2010 | Zhao et al. | |
| 7,720,538 B2 | 5/2010 | Janzig et al. | |
| 7,736,191 B1 | 6/2010 | Sochor | |
| 7,742,817 B2 | 6/2010 | Malinowski et al. | |
| 7,747,321 B2 | 6/2010 | Fischbach et al. | |
| 7,761,165 B1 | 7/2010 | He et al. | |
| 7,765,005 B2 * | 7/2010 | Stevenson | 607/37 |
| 7,794,256 B1 | 9/2010 | Sochor | |
| 7,901,761 B1 | 3/2011 | Jiang et al. | |
| 7,930,032 B2 | 4/2011 | Teske et al. | |
| 7,970,474 B2 | 6/2011 | Starke | |
| 7,989,080 B2 | 8/2011 | Greenberg et al. | |
| 8,000,804 B1 * | 8/2011 | Wessendorf et al. | 607/116 |
| 8,065,009 B2 | 11/2011 | Biggs | |
| 8,131,369 B2 | 3/2012 | Taylor et al. | |
| 8,131,376 B1 | 3/2012 | Faraji et al. | |
| 8,163,397 B2 | 4/2012 | Ok et al. | |
| 8,179,658 B2 * | 5/2012 | Brendel et al. | 361/302 |
| 8,288,654 B2 | 10/2012 | Taylor et al. | |
| 8,326,425 B2 | 12/2012 | Sprain et al. | |
| 8,346,362 B2 | 1/2013 | Kinney et al. | |
| 8,355,785 B1 | 1/2013 | Hammond et al. | |
| 8,378,239 B2 | 2/2013 | Lakner et al. | |
| 8,391,983 B2 | 3/2013 | Lim | |
| 8,494,635 B2 | 7/2013 | Troetzschel et al. | |
| 8,497,435 B2 | 7/2013 | Nagata et al. | |
| 8,528,201 B2 | 9/2013 | Troetzschel et al. | |
| 8,538,530 B1 | 9/2013 | Orinski | |
| 8,552,311 B2 | 10/2013 | Koester et al. | |
| 8,626,310 B2 | 1/2014 | Barror et al. | |
| 8,656,736 B2 | 2/2014 | Terao | |
| 8,659,870 B2 | 2/2014 | Brendel et al. | |
| 8,742,268 B2 | 6/2014 | Reisinger et al. | |
| 8,825,162 B2 | 9/2014 | Reisinger | |
| 8,894,914 B2 | 11/2014 | Pavlovic | |
| 9,032,614 B2 | 5/2015 | Specht | |
| 9,040,819 B2 | 5/2015 | Kempf et al. | |
| 9,048,608 B2 | 6/2015 | Pavlovic | |
| 9,088,093 B2 | 7/2015 | Reisinger et al. | |
| 2001/0013756 A1 | 8/2001 | Mori et al. | |
| 2004/0116976 A1 | 6/2004 | Spadgenske | |
| 2004/0128016 A1 | 7/2004 | Stewart | |
| 2006/0247714 A1 | 11/2006 | Taylor et al. | |
| 2006/0259093 A1 * | 11/2006 | Stevenson et al. | 607/37 |
| 2007/0183118 A1 | 8/2007 | Fu et al. | |
| 2008/0060834 A1 | 3/2008 | Eck et al. | |
| 2008/0060844 A1 | 3/2008 | Teske et al. | |
| 2008/0071313 A1 | 3/2008 | Stevenson et al. | |
| 2008/0119906 A1 * | 5/2008 | Starke | 607/36 |
| 2008/0203917 A1 | 8/2008 | Maya | |
| 2008/0269831 A1 | 10/2008 | Erickson | |
| 2009/0192578 A1 | 7/2009 | Biggs | |
| 2009/0281586 A1 | 11/2009 | Lim | |
| 2010/0023086 A1 | 1/2010 | Lim | |
| 2010/0109966 A1 | 5/2010 | Mateychuk et al. | |
| 2010/0258342 A1 | 10/2010 | Parker | |
| 2011/0034965 A1 * | 2/2011 | Troetzschel et al. | 607/37 |
| 2011/0034966 A1 | 2/2011 | Troetzschel et al. | |
| 2011/0048770 A1 | 3/2011 | Reiterer et al. | |
| 2011/0186349 A1 | 8/2011 | Troetzschel et al. | |
| 2012/0127627 A1 | 5/2012 | Brendel et al. | |
| 2012/0193117 A1 | 8/2012 | Specht et al. | |
| 2012/0193118 A1 | 8/2012 | Kempf et al. | |
| 2012/0193119 A1 | 8/2012 | Kempf et al. | |
| 2012/0193125 A1 | 8/2012 | Pavlovic et al. | |
| 2012/0193141 A1 | 8/2012 | Reisinger et al. | |
| 2012/0194981 A1 | 8/2012 | Kempf et al. | |
| 2012/0197326 A1 | 8/2012 | Pavlovic | |
| 2012/0197327 A1 | 8/2012 | Specht | |
| 2012/0197335 A1 | 8/2012 | Reisinger | |
| 2012/0200011 A1 | 8/2012 | Pavlovic | |
| 2012/0203294 A1 | 8/2012 | Troetzschel | |
| 2014/0262494 A1 | 9/2014 | Reisinger et al. | |
| 2014/0368298 A1 | 12/2014 | Reisinger | |
| 2015/0122875 A1 | 5/2015 | Pavlovic et al. | |

FOREIGN PATENT DOCUMENTS

| | | |
|---|---|---|
| DE | 102008021064 | 10/2009 |
| DE | 102009035971 | 2/2011 |
| DE | 102009035972 | 4/2011 |
| DE | 102010006837 | 8/2011 |
| DE | 102010006838 | 8/2011 |
| DE | 102010006689 | 9/2011 |
| DE | 102010006690 | 9/2011 |
| EP | 0877400 | 11/1998 |
| EP | 1685874 | 8/2006 |
| EP | 1754511 | 2/2007 |
| WO | 03073450 | 9/2003 |
| WO | 2004110555 | 12/2004 |
| WO | 2008103166 | 8/2008 |
| WO | 2010091435 | 8/2010 |

OTHER PUBLICATIONS

The Office Action for U.S. Appl. No. 13/361,340 mailed Oct. 25, 2013 (20 pages).

The Restriction Requirement for U.S. Appl. No. 13/361,348 mailed Nov. 14, 2013 (7 pages).

The Office Action for U.S. Appl. No. 13/361,355 mailed Aug. 7, 2013 (21 pages).

The Restriction Requirement for U.S. Appl. No. 13/361,362 mailed Nov. 14, 2013 (7 pages).

The Office Action for U.S. Appl. No. 13/361,370 mailed Oct. 29, 2013 (26 pages).

(56) References Cited

OTHER PUBLICATIONS

The Restriction Requirement for U.S. Appl. No. 13/361,383 mailed Feb. 27, 2013 (6 pages).
The Office Action for U.S. Appl. No. 13/361,383 mailed Nov. 13, 2013 (22 pages).
The Restriction Requirement for U.S. Appl. No. 13/361,404 mailed Apr. 8, 2013 (6 pages).
The Restriction Requirement for U.S. Appl. No. 13/361,404 mailed Oct. 9, 2013 (5 pages).
The Notice of Allowance for U.S. Appl. No. 13/361,355 mailed Jan. 16, 2014 (18 pages).
The Office Action for U.S. Appl. No. 13/361,322 mailed date Feb. 19, 2014 (26 pages).
The Office Action for U.S. Appl. No. 13/361,340 mailed date Apr. 29, 2014 (18 pages).
The Office Action for U.S. Appl. No. 13/361,348 mailed date Feb. 19, 2014 (23 pages).
The Office Action for U.S. Appl. No. 13/361,362 mailed date Feb. 19, 2014 (19 pages).
The Office Action for U.S. Appl. No. 13/361,370 mailed date May 14, 2014 (18 pages).
The Notice of Allowance for U.S. Appl. No. 13/361,383 mailed date Apr. 25, 2014 (18 pages).
The Office Action for U.S. Appl. No. 13/361,388 mailed date Feb. 11, 2014 (24 pages).
The Office Action for U.S. Appl. No. 13/361,398 mailed date Mar. 7, 2014 (26 pages).
The Office Action for U.S. Appl. No. 13/361,404 mailed date Feb. 27, 2014 (19 pages).
The Restriction Requirement for U.S. Appl. No. 13/361,411 mailed date Mar. 10, 2014 (7 pages).
The Final Office Action for U.S. Appl. No. 13/361,322 mailed date Sep. 9, 2014 (17 pages).
The Final Office Action for U.S. Appl. No. 13/361,340 mailed date Oct. 30, 2014 (21 pages).
The Final Office Action for U.S. Appl. No. 13/361,348 mailed date Sep. 9, 2014 (19 pages).
The Final Office Action for U.S. Appl. No. 13/361,362 mailed date Sep. 9, 2014 (19 pages).
The Final Office Action for U.S. Appl. No. 13/361,370 mailed date Nov. 5, 2014 (19 pages).
The Office Action for U.S. Appl. No. 13/361,388 mailed date Jul. 31, 2014 (32 pages).
The Notice of Allowance for U.S. Appl. No. 13/361,398 mailed date Jul. 25, 2014 (11 pages).
The Final Office Action for U.S. Appl. No. 13/361,404 mailed date Oct. 9, 2014 (12 pages).
The Office Action for U.S. Appl. No. 13/361,411 mailed date Aug. 1, 2014 (18 pages).
The Office Action for U.S. Appl. No. 13/361,322 mailed date Feb. 4, 2015 (19 pages).
The Office Action for U.S. Appl. No. 13/361,340 mailed Mar. 12, 2015 (23 pages).
The Notice of Allowance for U.S. Appl. No. 13/361,348 mailed Jan. 22, 2015 (9 pages).
The Notice of Allowance for U.S. Appl. No. 14/293,596 mailed Mar. 17, 2015 (28 pages).
The Notice of Allowance for U.S. Appl. No. 13/361,370 mailed May 1, 2015 (17 pages).
The Office Action for U.S. Appl. No. 13/361,388 mailed Feb. 9, 2015 (29 pages).
Hussain, et al., "Electrical conductivity of an insulator matrix (alumina) and conductor particle (molybdenum) composites", Journal of the European Ceramic Society, vol. 23, Issue 2, Feb. 2003, pp. 315-321.
The Notice of Allowance for U.S. Appl. No. 13/361,404 mailed Jan. 28, 2015 (6 pages).
The Notice of Allowance for U.S. Appl. No. 13/361,411 mailed Jan. 20, 2015 (8 pages).
The Final Office Action for U.S. Appl. No. 13/361,322 dated Aug. 24, 2015 (21 pages).

* cited by examiner

CERAMIC BUSHING WITH FILTER

CROSS-REFERENCE TO RELATED APPLICATIONS

This Non-Provisional patent application claims the benefit of the filing date of U.S. Provisional Patent Application Ser. No. 61/438,042, filed Jan. 31, 2011, entitled "CERAMIC BUSHING WITH FILTER," and this patent application also claims priority to German Patent Application No. DE 10 2011 009 859.3, filed on Jan. 31, 2011, and both of which are incorporated herein by reference.

This Patent Application is also related to patent application Ser. No. 13/361,322 filed on Jan. 30, 2012, entitled "CERAMIC BUSHING FOR AN IMPLANTABLE MEDICAL DEVICE"; patent application Ser. No. 13/361,340 filed on Jan. 30, 2012, entitled "DIRECTLY APPLICABLE ELECTRICAL BUSHING"; patent application Ser. No. 13/361,348 filed on Jan. 30, 2012, entitled "IMPLANTABLE DEVICE HAVING AN INTEGRATED CERAMIC BUSHING"; patent application Ser. No. 13/361,355 filed on Jan. 30, 2012, entitled "HEAD PART FOR AN IMPLANTABLE MEDICAL DEVICE"; patent application Ser. No. 13/361,362 filed on Jan. 30, 2012, entitled "CERMET-CONTAINING BUSHING FOR AN IMPLANTABLE MEDICAL DEVICE HAVING A CONNECTING LAYER"; patent application Ser. No. 13/361,370 filed on Jan. 30, 2012, entitled "ELECTRICAL BUSHING WITH CERMET-CONTAINING CONNECTING ELEMENT FOR AN ACTIVE IMPLANTABLE MEDICAL DEVICE"; patent application Ser. No. 13/361,383 filed on Jan. 30, 2012, entitled "CERAMIC BUSHING WITH INDUCTIVE FILTER"; patent application Ser. No. 13/361,388 filed on Jan. 30, 2012, entitled "CERAMIC BUSHING HAVING HIGH CONDUCTIVITY CONDUCTING ELEMENTS"; patent application Ser. No. 13/361,398 filed on Jan. 30, 2012, entitled "METHOD FOR THE MANUFACTURE OF A CERMET-CONTAINING BUSHING"; patent application Ser. No. 13/361,404 filed on Jan. 30, 2012, entitled "METHOD FOR THE MANUFACTURE OF A CERMET-CONTAINING BUSHING FOR AN IMPLANTABLE MEDICAL DEVICE"; and patent application Ser. No. 13/361,411 filed on Jan. 30, 2012, entitled "CERMET-CONTAINING BUSHING WITH HOLDING ELEMENT FOR AN IMPLANTABLE MEDICAL DEVICE".

BACKGROUND

One aspect relates to an electrical bushing for use in a housing of an implantable medical device. Moreover, one aspect relates to a method for the manufacture of an electrical bushing for an implantable medical device.

The post-published document, DE 10 2009 035 972, discloses an electrical bushing for an implantable medical device having the features of the preamble of claim 1. Moreover, a use of at least one cermet-including conducting element in an electrical bushing for an implantable medical device and a method for the manufacture of an electrical bushing for an implantable medical device are disclosed.

A multitude of electrical bushings for various applications are known, examples including: U.S. Pat. No. 4,678,868, U.S. Pat. No. 7,564,674 B2, US 2008/0119906 A1, U.S. Pat. No. 7,145,076 B2, U.S. Pat. No. 7,561,917, US 2007/0183118 A1, U.S. Pat. No. 7,260,434B1, U.S. Pat. No. 7,761,165, U.S. Pat. No. 7,742,817 B2, U.S. Pat. No. 7,736,191 B1, US 2006/0259093 A1, U.S. Pat. No. 7,274,963 B2, US 2004116976 A1, U.S. Pat. No. 7,794,256, US 2010/0023086 A1, U.S. Pat. No. 7,502,217 B2, U.S. Pat. No. 7,706,124 B2, U.S. Pat. No. 6,999,818 B2, EP 1754511 A2, U.S. Pat. No. 7,035,076, EP 1685874 A1, WO 03/073450 A1, U.S. Pat. No. 7,136,273, U.S. Pat. No. 7,765,005, WO 2008/103166 A1, US 2008/0269831, U.S. Pat. No. 7,174,219 B2, WO 2004/110555 A1, U.S. Pat. No. 7,720,538 B2, WO 2010/091435, US 2010/0258342 A1, US 2001/0013756 A1, U.S. Pat. No. 4,315,054, and EP 0877400.

DE 697 297 19 T2 describes an electrical bushing for an active implantable medical device—also called implantable device or therapeutic device. Electrical bushings of this type serve to establish an electrical connection between a hermetically sealed interior and an exterior of the therapeutic device. Known implantable therapeutic devices are cardiac pacemakers or defibrillators, which usually include a hermetically sealed metal housing which is provided with a connection body, also called header, on one of its sides. Said connection body includes a hollow space having at least one connection socket for connecting electrode leads. In this context, the connection socket includes electrical contacts in order to electrically connect the electrode leads to the control electronics on the interior of the housing of the implantable therapeutic device. Hermetic sealing with respect to a surrounding is an essential prerequisite of an electrical bushing of this type. Therefore, lead wires that are introduced into an electrically insulating base body—also called signal-transmission elements—through which the electrical signals are propagated, must be introduced into the base body such as to be free of gaps. In this context, it has proven to be challenging that the lead wires generally are made of a metal and are introduced into a ceramic base body. In order to ensure a durable connection between the two elements, the internal surface of a through-opening—also called openings—in the base body is metallized for attachment of the lead wires by soldering. However, the metallization in the through-opening has proven to be difficult to apply. Only expensive procedures ensure homogeneous metallization of the internal surface of the bore hole and thus a hermetically sealed connection of the lead wires to the base body by soldering. The soldering process itself requires additional components, such as solder rings. Moreover, the process of connecting the lead wires to the previously metallized insulators utilizing the solder rings is a process that is laborious and difficult to automate.

Printed publication U.S. Pat. No. 7,564,674 B2 describes a bushing for implantable devices, in which connection pins made of metal extend through an opening of an insulator. The insides of the openings are metallized for connection of the connecting pins to the insides of the openings using solder. The bushing further includes a filter capacitor, which likewise includes openings with metallized insides, whereby the connection pins likewise extend through said openings and are connected to them by means of solder. Connecting the filter capacitor to the connection pins necessitates an additional solder step during the manufacture. As a result, there are multiple connections concerning a multitude of components which have to be established through soldering. This not only renders the manufacturing method highly complex, but also makes the manufacture highly error-prone since the soldering steps concern different components, which each must be soldered in a certain way only. Due, for example, to the proximity to each other of the various components to be soldered, there is a risk that undesired solder connections may arise, even more so since previously established solder connections are partially melted again in each step of soldering.

For these and other reasons there is a need for the present invention.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Further measures and advantages of the invention are evident from the claims, the description provided hereinafter, and the drawings. The invention is illustrated through several exemplary embodiments in the drawings. In this context, equal or functionally equal or functionally corresponding elements are identified through the same reference numbers. The invention shall not be limited to the exemplary embodiments.

DETAILED DESCRIPTION

Figure 1:
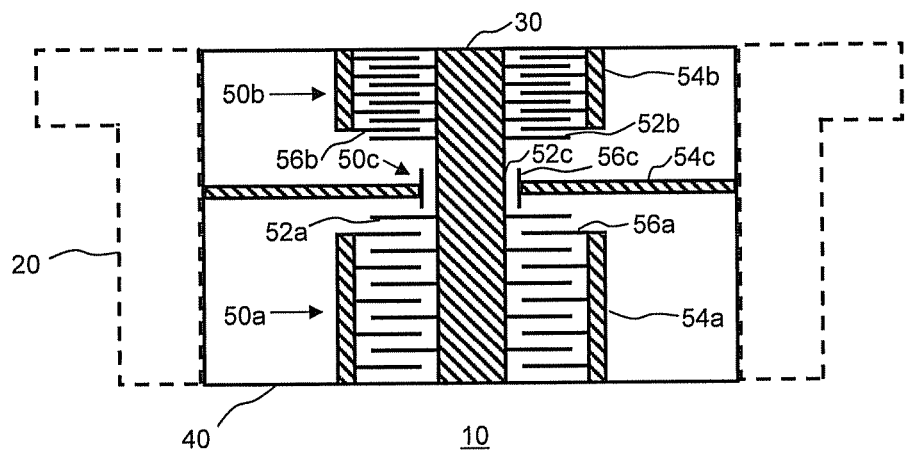
FIG. 1 illustrates a first embodiment of an electrical bushing with multiple variants of filter structures.

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

It is to be understood that the features of the various exemplary embodiments described herein may be combined with each other, unless specifically noted otherwise.

One embodiment creates an electrical bushing for an implantable medical device, in which at least one of the disadvantages mentioned above is prevented at least in part. One embodiment provides a bushing having a filter that can be manufactured easily, at high precision, and low reject rates. Features and details that are described in the context of the electrical bushing or the implantable medical device shall also apply in relation to the method, and vice versa.

The electrical bushing according to one embodiment is designed for use in a housing of an implantable medical device. The electrical bushing includes at least one electrically insulating base body. Moreover, the electrical bushing includes at least one electrical conducting element. The conducting element is set up to establish, through the base body, at least one electrically conductive connection between an internal space of the housing and an external space. In one embodiment, the electrical connection proposed in this context is an ohmic connection with low resistance—for example, for a direct current signal—, that is, a resistance of, for example, no more than 10 Ohm, 1 Ohm, 100 mOhm, 10 mOhm or 1 mOhm. The conducting element extends through the base body, that is, along the direction of the longitudinal extension thereof. The conducting element can extend along a straight line. In one embodiment, the conducting element extends along or parallel to a longitudinal axis of the base body. The conducting element can be provided as a single part or multiple parts and can include intermediary electrical elements that provide a section of the electrically conductive connection. The conducting element can include a connecting surface that is directly adjacent to the internal space as well as a connecting surface that is directly adjacent to the external space, which serve for contacting the conducting element.

The conducting element is hermetically sealed with respect to the base body. Accordingly, conducting element and base body can include a common boundary surface. A seal is formed at the boundary surface and provides the hermetical sealing.

The at least one conducting element includes at least one cermet. The cermet forms a continuous structure, for example, in the longitudinal direction of the conducting element. Said structure forms at least sections of the electrically conductive connection. The cermet has high specific conductivity in one embodiment of at least 1, at least 100, at least $10^3$, at least $10^4$, and in one embodiment at least $10^5$ or $10^6$ S/m.

The base body is made from the insulating material either in part or fully. Said material corresponds to the at last one insulating material of the base body as described herein.

According to one embodiment, the electrical bushing includes an electrical filter structure. The at least one conducting element forms at least one electrically conducting surface of the filter structure. Since the conducting element therefore forms not only the electrically conductive connection between the internal space and the external space of the housing and also forms a component of the filter structure, that is, the at least one electrically conductive surface, the resulting manufacturing process is simplified and the degree of integration is increased.

The electrical filter structure forms an electrical filter. The electrical filter structure is connected to the electrically conductive connection which is established through the conducting element. An electrical filter structure shall be understood to be a network that has different impedances for different frequencies of a signal that is applied to the filter structure. The electrical filter structure is set up to provide different attenuations for different frequency components of a signal that is transmitted by the electrically conductive connection. The correlation of frequency and attenuation is also called frequency selectivity.

One embodiment of one embodiment provides the filter structure to include a capacitor or an electromechanical resonator. The at least one electrically conductive surface of the filter structure forms an electrode surface. The electrically conductive surface, for example, forms a filter structure of the capacitor or of the electromechanical resonator. The electrode surface therefore forms at least one electrode of the capacitor or of the electromechanical resonator. The electrode surface forms at least one electrode that is set up to generate an electrical field, for example opposite to another electrode or another conductive surface. The electrical field extends through the space adjacent to the electrode. In the case of a capacitor, the electrode surface generates, according to its potential, an electrical field in the space bordering on the electrode surface, which stores energy. In the case of an electromechanical resonator, the electrode surface generates, according to the signal applied to it, an electrical field in a piezoceramic unit that is situated in the space bordering on the electrode surface. In this context, the electrode surface is set up to convert, in conjunction with the piezoceramic unit, the electrical energy into acoustical energy that is transmitted to and/or stored in the piezoceramic unit. The electrode surface forms a component of a frequency-selective component, whereby the frequency-selective component can be provided, for example, as capacitor or electromechanical resonator.

One section of the electrically insulating base body forms a dielectric layer of the capacitor. In this context, the electrically insulating base body forms a dielectric of the capacitor in order to increase the permittivity of the capacitor as compared to a capacitor in a vacuum. Alternatively, a section of the electrically insulating base body forms a piezoelectric body of the electromechanical resonator. The section of the electrically insulating base body is thus provided as electromechanical resonator. The two preceding options can just as well be used in combination. In both cases, the base body assumes, aside from the function as electrical insulator, a further function in that the section of the electrically insulating base body provides a part of a frequency-selective component. In this context, the frequency-selective component is, for example, a capacitor or an electromechanical resonator. The electromechanical resonator can be provided as crystal oscillator, SAW filter or BAW filter.

The at least one electrically conductive surface of the filter structure forms multiple electrode surfaces of the capacitor. The electrode surfaces in one embodiment belong to two different polarities of the capacitor, are in one embodiment not directly connected to each other in an electrically conductive manner, and are set up, for example, to generate an electrical field in the space between the electrode surfaces when a voltage is applied to the capacitor. Moreover, one embodiment provides multiple electrode surfaces to extend plane parallel to each other. The conducting element further includes at least one connecting section that extends from one of the electrode surfaces to at least one other electrode surface in order to electrically connect them. The electrode surfaces connected electrically through the at least one connecting section belong to the same pole—that is, the same connector—of the capacitor. In one embodiment, the capacitor includes at least two different poles which each include multiple electrode surfaces, whereby the electrode surfaces of each pole are electrically connected to each other through corresponding connecting sections. The electrode surfaces provided by the conducting element form a multi-layer stack, whereby a dielectric each is provided between two neighboring electrode surfaces. The dielectric in one embodiment is provided in each case through sections of the base body. The electrode surfaces are assigned in an alternating manner to two different poles of the capacitor and are electrically connected to same, for example, through the connecting sections. The electrode surfaces and the connecting sections form a double-comb structure with two interdigitating comb structures. The structure of the electrode surfaces and connecting sections corresponds to the conductor and dielectric structure of a multi-layer capacitor.

In another embodiment, the filter structure includes a frequency-selective component. The frequency-selective component can be a separate component or an integrated component whose electrical or electronic components are accommodated in a separate housing of the component. The frequency-selective component forms an independent component and forms an independent body. The frequency-selective component can, for example, be pre-fabricated and in one embodiment corresponds to a standardized design, for example a design according to a JEDEC standard. The frequency-selective components are, for example, SMD elements. The at least one electrically conductive surface of the filter structure forms at least one contact surface. The component is connected to said contact surface. The frequency-selective component is provided, for example, as capacitor, as inductor, as electromechanical resonator, for example, in the form of a BAW filter, a SAW filter, or a crystal oscillator or as an integrated filter circuit. The frequency-selective component can be provided, for example, as capacitor, as capacitor with ceramic or mica as dielectric.

Moreover, the capacitor can be provided as foil-type capacitor, metallized paper capacitor, electrolyte capacitor—for example, as tantalum capacitor—or just as well as a double-layer capacitor. Providing the frequency-selective component as capacitor can include one or more capacitors that can be connected to each other. Providing the frequency-selective component as inductor, the frequency-selective component includes at least one winding of a coil. The inductor can be provided, for example, with or without core. In one embodiment, the inductor is provided as a wire coil with one or more windings, whereby the wire can be provided as bare wire or coated by an electrically insulating layer of varnish. In this context, litz wire can be used instead of wire. The coil of the inductor is provided to be, for example, made of metal or a metal alloy. In one embodiment, the material providing the coil has a melting point above 700° C., above 800° C., above 1,000° C. or above 1,200° C.

Moreover, the frequency-selective component can be provided as electromechanical resonator. The electromechanical resonator includes a piezoelectric body on which electrodes are provided. Due to the piezoelectric properties, electrical energy is converted into acoustical energy, whereby the structure of the electromechanical resonator defines an oscillation mode, for example surface oscillations or oscillations that are propagated through the piezoelectric body. SAW filters, which are also called acoustical surface filters, are specific electromechanical resonators. Moreover, the electromechanical resonator can be provided as BAW filter (bulk acoustic wave filter). Moreover, the electromechanical resonator can be provided as crystal oscillator. In the case of the BAW filter and the crystal oscillator, the piezoelectric body is acoustically insulated with respect to a housing of the component.

Moreover, the component can be provided as an integrated filter circuit that integrates multiple individual electrical or electronic components. For example, the integrated filter circuit can include passive components, for example at least one capacitor and at least one inductor, for example a choke. Moreover, the integrated filter circuit can include at least one active component, for example a transistor.

The at least one contact surface is part of the filter structure. The contact surface is connected, for example, to the frequency-selective component and thus forms an electrical connection to the frequency-selective component which is a part of the filter structure as well.

The frequency-selective component includes a connector. The connector is physically connected to the contact surface through a solder connection or by means of a press-fit. The connector of the frequency-selective component can border directly on the contact surface or be connected to it through a firmly bonded, electrically conductive connection. The at least one connector of the frequency-selective component is connected to the at least one contact surface that is provided by the cermet through an electrical connection that can be provided as firmly bonded, positive fit-type or non-positive fit-type connection. The at least one connector of the frequency-selective component can be provided as an electrically conductive connection surface or as a piece of wire and/or as a pin.

According to a specific embodiment, the at least one conductive surface extends parallel or perpendicular to a longitudinal extension of the base body. In this context, the electrically conductive surface can be provided as at least one electrode surface or as at least one contact surface. The direction of the longitudinal extension of the base body corresponds to the extension of a straight line through a housing wall of the housing into which the electrical bushing can be inserted. The at least one electrically conductive surface is essentially planar, that is, it extends along a plane, or is essentially convex or circular cylinder-shaped. Moreover, the electrically conductive surface can extend along a section of a circular cylinder or along a section of a sphere. In the latter case, the at least one electrically conductive surface has a spherical cap profile. The above-mentioned shapes are the shapes of an electrically conductive surface, whereby, in case multiple electrically conductive surfaces being provided, each surface takes said shape.

Another embodiment provides the electrical bushing to include multiple conducting elements. The multiple conducting elements each form a conductive surface of the filter structure. In this context, all conductive surfaces of the conducting element and/or conducting elements of an electrical bushing can form electrode surfaces or contact surfaces. This applies, for example, to front surfaces or circumferential surfaces of the at least one conducting element. Moreover, the conductive surfaces of at least one of the conducting elements can form electrode surfaces or contact surfaces, whereas the remaining conductive surfaces of the multiple conducting elements form contact surfaces or electrode surfaces. Some of the conducting elements or all conducting elements extend parallel to each other. Some or all conducting elements of the bushing are arranged to be equidistant to each other, in one embodiment in the form of a row or in the form of multiple, equidistant rows. At least one electrical bushing according to one embodiment can include at least 2, 5, 10, 20, 50, 100, 200, 500 or 1000 conducting elements. The conducting elements are in one embodiment not directly electrically connected to each other. The conducting elements each form an individual electrical connection. The electrical bushing can include one or more filter structures. A filter structure can be provided for two or more conducting elements of the electrical bushing.

The filter structure and/or the at least one electrically conductive surface can be arranged on a surface of the bushing. Said surface borders on the internal space or on the external space between which an electrically conductive connection is established by the conducting element. Alternatively, the filter structure and/or the at least one electrically conductive surface can be arranged inside the bushing. The filter structure, one electrode forming the electrode surface or a contact forming the contact surface can be coated with a protective layer which is in one embodiment electrically insulating. Said protective layer forms an insulating body with respect to the internal space or the external space that borders on the protective layer.

The filter structure of the electrical bushing can include one or more electrical components, whereby the components are selected from the group consisting of capacitor, electromechanical resonator or frequency-selective component, whereby said components each are provided as described above. The filter structure in one embodiment provides a band-stop filter or a low-pass filter. The filter structure can include a capacitive feedthrough filter, a parallel dissipation capacitor, a serial filter inductor, an LC anti-resonant circuit, an LC resonant circuit, a continuity filter in a T arrangement or a π arrangement, an electromechanical dissipation filter or an electromechanical serial filter. The LC anti-resonant circuit is arranged in series to the electrically conductive connection between the internal space and the external space. The LC resonant circuit is connected to the electrically conductive connection between the internal space and the external space as a dissipation filter. The continuity filter in a T-arrangement includes two serial inductors and a parallel capacitor arranged in between. The continuity filter in a π-arrangement includes two parallel capacitors and a serial inductor arranged in between.

Either an electrically conductive holding element that extends around the electrical bushing or an electrical connector that is set up to be electrically connected to the housing can serve for dissipation. Moreover, the housing or a connection to the housing can serve for dissipation. The above-mentioned variants of circuits that can be provided by the filter structure are illustrated in more detail in the figures.

Moreover, the base body and the at least one conducting element are provided to be connected to each other in a firmly bonded manner, for example, through a firmly bonded sintered connection. Moreover, the base body and the at least one conducting element can be connected to each other in a firmly bonded manner through an electrically conductive soldered connection or through a glass solder connection. For example, a hard solder connection can connect the base body to the at least one conducting element in a firmly bonded manner.

Moreover, in one embodiment relates to an implantable medical device, for example, a cardiac pacemaker or defibrillator, whereby the implantable medical device includes at least one electrical bushing according to one embodiment.

Moreover, one embodiment provides a housing for use for an implantable medical device, whereby the housing includes at least one electrical bushing. Both the housing and the device include an internal space, whereby the housing and the device enclose the internal space.

One embodiment is also implemented through the use of at least one cermet-including conducting element in an electrical bushing for an implantable medical device. The conducting element is provided to provide at least one electrically conductive surface of an electrical filter structure of the bushing. For example, the conducting element including the cermet is provided, for example, to form at least one electrode structure of the filter structure or at least one contact surface of the filter structure. Likewise, the scope of one embodiment includes the use of a cermet for providing an electrical bushing for an implantable medical device and for providing at least one electrically conductive surface of an electrical filter structure. In this context, the filter structure, the electrically conductive surface, the electrode surface and/or the contact surface correspond to the corresponding components of the electrical bushing described above.

And lastly, one embodiment is implemented through a method for the manufacture of an electrical bushing for an implantable medical device. The method includes the following steps:

a. generating at least one base body green compact for at least one base body from an electrically insulating material;

b. forming at least one cermet-containing conducting element green compact for at least one conducting element;

c. introducing the at least one conducting element green compact into the base body green compact;

d. subjecting the insulation element green compact with the at least one base body green compact to firing in order to obtain at least one base body with at least one conducting element.

Moreover, the method includes a step of providing an electrical filter structure. Step b. includes the forming of at least one electrically conductive surface of the filter structure.

The steps a. and b. can be carried out simultaneously or in any order. Moreover, step b. can be carried out before step c. in order to form the conducting element green compact before introducing it into the base body green compact. Alternatively, step b. can be carried out during step c., whereby the cermet-containing conducting element green compact is formed while it is introduced. Accordingly, the at least one electrically conductive surface of the electrical filter structure can be formed before or during the insertion of the conducting element green compact into the base body. The at least one electrically conductive surface of the electrical filter structure is formed before providing the electrical filter structure, while providing the electrical filter structure or after partially or fully providing the electrical filter structure.

The method for manufacture can, for example, include further firing steps, in which the conducting element green compact, the base body green compact, parts of the electrical filter structure, the entire electrical filter structure and/or the electrically conductive surface are pre-sintered in order to obtain pre-sintered green compacts, filter structure parts, a pre-sintered filter structure or a pre-sintered electrically conductive surface. Moreover, the method can provide that a holding element green compact, which surrounds the base body or the base body green compact, is provided or formed, for example, from electrically conductive or electrically insulating material.

Step a. can include a partial sintering of the base body green compact. In combination or alternatively, step b. can include a partial sintering of the conducting element green compact.

The electrically insulating material of the base body or base body green compact includes or essentially consists of the materials described above as the at least one material of the base body.

In one embodiment, the at least one cermet-containing conducting element green compact and the at least one electrically conductive surface of the electrical filter structure are formed through the same step of forming. The electrical filter structure is, for example in one embodiment, provided through the same steps used to generate the base body green compact and to form the conducting element green compact.

Further embodiments of the method provide that a holding element green compact is produced that can, for example, be partially sintered. In one embodiment, the holding element green compact is partially sintered after forming it around the pre-sintered or non-pre-sintered base body green compact. The holding element and/or the holding element green compact includes a cermet.

In one embodiment, the electrically insulating material is one electrically insulating material or a composition of materials. The composition of materials includes at least one element from the group consisting of aluminum oxide, magnesium oxide, zirconium oxide, aluminum titanate, and piezoceramic materials.

Another embodiment of the method entails that the step of providing the filter structure includes: providing a capacitor or an electromechanical resonator. The at least one electrical surface is provided as electrode surface of the capacitor or of the electromechanical resonator, for example, by planar forming Step a. further includes providing a section of the base body as dielectric layer of the capacitor or as piezoelectric body of the electromechanical resonator. The electrode surface is then applied onto the dielectric layer and/or the piezoelectric body, in one embodiment in step c. The section of the base body is in one embodiment provided as green compact. After the provision of said green compact follows a sintering step, in which at least the base body is sintered.

And lastly, an embodiment of the method entails that the step of providing the filter structure includes: providing the electrically conductive surface as at least one contact surface. The method further provides for inserting at least one pre-fabricated frequency-selective component into the conducting element green compact or into the base element green compact. The component corresponds to the frequency-selective component that was illustrated above in the context of the electrical bushing. Moreover, the at least one frequency-selective component is provided to be connected to the at least one contact surface. The frequency-selective component is introduced and connected before or after the conducting element green compact is introduced into the base body green compact. The inserting and the connecting can be carried out as a single step. Alternatively, the method can provide for arranging at least one pre-fabricated frequency-selective component on or in the base body and connecting it to the conducting element after step d. of firing has been carried out. For example, the component is arranged on or in the base body after pre-sintering steps, if any, have been completed. Furthermore, the connecting of the component can be provided through attaching at least one connector of the component by soldering or by plugging-in the component in order to electrically connect it to the bushing.

Accordingly, the frequency-selective component is co-sintered with at least one of the green compacts or the component is inserted after all sintering steps are completed. The latter option is used in case the frequency-selective component is unsuitable for high temperatures and exposing the component to the sintering temperature would destroy or damage the component.

The electrode surface and contact surface described in the scope of the method can be provided in accordance with the electrode surface and/or contact surface described herein in the description of the electrical bushing.

The proposed electrical bushing is set up for use in an implantable medical device, whereby the implantable medical device can be provided, for example, as an active implantable medical device (AIMD) and in one embodiment as a therapeutic device.

As a matter of principle, the term, implantable medical device, shall include any device which is set up to perform at least one medical function and which can be introduced into a body tissue of a human or animal user. As a matter of principle, the medical function can include any function selected from the group consisting of a therapeutic function, a diagnostic function, and a surgical function. For example, the medical function can include at least one actuator function, in which an actuator is used to exert at least one stimulus on the body tissue, for example, an electrical stimulus.

As a matter of principle, the term, active implantable medical device—also called AIMD—shall include all implantable medical devices that can conduct electrical signals from a hermetically sealed housing to a part of the body tissue of the user and/or receive electrical signals from the part of the body tissue of the user. Accordingly, the term, active implantable medical device, includes, for example, cardiac pacemakers, cochlea implants, implantable cardioverters/defibrillators, nerve, brain, organ or muscle stimulators as well as implantable monitoring devices, hearing aids, retinal implants, muscle stimulators, implantable drug pumps, artificial hearts, bone growth stimulators, prostate implants, stomach implants or the like.

The implantable medical device, for example, the active implantable medical device, can usually include, for example, at least one housing, for example, at least one hermetically sealed housing. The housing can in one embodiment enclose at least one electronics unit, for example a triggering and/or analytical electronics unit of the implantable medical device.

In the scope of one embodiment, a housing of an implantable medical device shall be understood to be an element that encloses, at least in part, at least one functional element of the implantable medical device that is set up to perform the at least one medical function or promotes the medical function. For example, the housing includes at least one internal space that takes up the functional element fully or in part. For example, the housing can be set up to provide mechanical protection to the functional element with respect to strains occurring during operation and/or upon handling, and/or provide protection to the functional element with respect to ambient influences such as, for example, influences of a body fluid. The housing can, for example, border and/or close the implantable medical device with respect to the outside.

In this context, an internal space shall be understood herein to mean a region of the implantable medical device, for example, within the housing, which can take up the functional element fully or in part and which, in an implanted state, does not contact the body tissue and/or a body fluid. The internal space can include at least one hollow space which can be closed fully or in part. However, alternatively, the internal space can be filled up fully or in part, for example by the at least one functional element and/or by at least one filling material, for example at least one casting, for example at least one casting material in the form of an epoxy resin or a similar material.

An external space, in contrast, shall be understood to be a region outside of the housing. This can, for example, be a region which, in the implanted state, can contact the body tissue and/or a body fluid. Alternatively or in addition, the external space can just as well be or include a region that is only accessible from outside the housing without necessarily contacting the body tissue and/or the body fluid, for example a region of a connecting element of the implantable medical device that is accessible from outside to an electrical connecting element, for example an electrical plug connector.

The housing and/or, for example, the electrical bushing can, for example, be provided to be hermetically sealed such that, for example, the internal space, is hermetically sealed with respect to the external space. In this context, the term, "hermetically sealed", can illustrate that moisture and/or gases cannot permeate through the hermetically sealed element at all or only to a minimal extent upon intended use for the common periods of time (for example 5-10 years). The leakage rate, which can be determined, for example, by leak tests, is a physical parameter that can described, for example, a permeation of gases and/or moisture through a device, for example, through the electrical bushing and/or the housing. Pertinent leak tests can be carried out with helium leak testers and/or mass spectrometers and are specified in the Mil-STD-883G Method 1014 standard. In this context, the maximal permissible helium leak rate is determined as a function of the internal volume of the device to be tested. According to the methods specified in MIL-STD-883G, method 1014, section 3.1 and taking into consideration the volumes and cavities of the devices to be tested that are used in the application of one embodiment, said maximal permissible helium leak rates can, for example, be from $1\times10^{-8}$ atm*cm$^3$/sec to $1\times10^{-7}$ atm*cm$^3$/sec. In the scope of one embodiment, the term, "hermetically sealed", shall be understood, for example, to mean that the device to be tested (for example the housing and/or the electrical bushing and/or the housing with the electrical bushing) has a helium leak rate of less than $1\times10^{-7}$ atm*cm$^3$/sec. In one embodiment, the helium leak rate can be less than $1\times10^{-8}$ atm*cm$^3$/sec, for example, less than $1\times10^{-9}$ atm*cm$^3$/sec. For the purpose of standardization, the above-mentioned helium leak rates can also be converted into the equivalent standard air leak rate. The definition of the equivalent standard air leak rate and the conversion are specified in the ISO 3530 standard.

Electrical bushings are elements set-up to generate at least one electrically conductive path (that is, an electrically conductive connection) that extends between the internal space of the housing to at least one external point or region outside the housing, for example, situated in the external space. The electrical bushings are, for example, elements which are set-up to generate the at least one electrically conductive path based on their resistivity and structure. Accordingly, this establishes, for example, an electrical connection to leads, electrodes, and sensors that are arranged outside the housing.

Common implantable medical devices are commonly provided with a housing, which can include, on one side, a head part, also called header or connecting body, that carries connection sockets for connection of leads, also called electrode leads. The connection sockets include, for example, electrical contacts that serve to electrically connect the leads to a control electronics unit on the interior of the housing of the medical device. Usually, an electrical bushing is provided in the location, at which the electrical connection enters into the housing of the medical device, and the electrical bushing is inserted into a corresponding opening of the housing in a hermetically sealing manner.

Due to the type of use of implantable medical devices, their hermetic sealing and biocompatibility are usually amongst the foremost requirements. The implantable medical device proposed herein according to one embodiment, can be inserted, for example, into a body of a human or animal user, for example, of a patient. As a result, the implantable medical device is usually exposed to a fluid of a body tissue of the body. Accordingly, it is usually important that no body fluid penetrates into the implantable medical device and that no liquids leak from the implantable medical device. In order to ensure this, the housing of the implantable medical device, and thus the electrical bushing as well, should be as impermeable as possible, for example, with respect to body fluids.

Moreover, the electrical bushing should ensure high electrical insulation between the at least one conducting element and the housing and/or the multiple conducting elements provided that more than one conducting element are present. In this context, the insulation resistance reached in one embodiment is at least several MOhm, in one embodiment, more than 20 MOhm, and the leakage currents reached can be small, in one embodiment, less than 10 pA. Moreover, in case multiple conducting elements are present, the crosstalk and electromagnetic coupling between the individual conducting elements in one embodiment are below the specified thresholds for medical applications.

The electrical bushing disclosed according to one embodiment is well-suited for the above-mentioned applications. Moreover, the electrical bushing can also be used in other applications that are associated with special requirements with regard to biocompatibility, tight sealing, and stability.

The electrical bushing according to one embodiment can meet, for example, the above-mentioned tight sealing requirements and/or the above-mentioned insulation requirements.

As mentioned above, the electrical bushing includes at least one electrically insulating base body. In the scope of one embodiment, a base body shall be understood to mean an element that serves a mechanical holding function in the electrical bushing, for example in that the base body holds or carries the at least one conducting element either directly or indirectly. For example, the at least one conducting element can be embedded in the base body directly or indirectly, fully or partly, for example, through a firmly bonded connection between the base body and the conducting element and in one embodiment through co-sintering of the base body and the conducting element. For example, the base body can have at least one side facing the internal space and at least one side facing the external space and/or accessible from the external space.

As mentioned above, the base body is provided to be electrically insulating. This means that the base body, fully or at least regions thereof, is made from at least one electrically insulating material. In this context, an electrically insulating material shall be understood to mean a material with a resistivity of at least $10^7$ Ohm*m, for example, of at least $10^8$ Ohm*m, in one embodiment of at least $10^9$ Ohm*m, and in one embodiment of at least $10^{11}$ Ohm*m. For example, the base body can be provided such that, as mentioned above, a flow of current between the conducting element and the housing and/or between multiple conducting elements is at least largely prevented, for example through the resistivity values between the conducting element and the housing as specified above being implemented. For example, the base body can include at least one ceramic material.

In this context, a conducting element or electrical conducting element shall generally be understood to mean an element set up to establish an electrical connection between at least two sites and/or at least two elements. For example, the conducting element can include one or more electrical conductors, for example metallic conductors. In the scope of one embodiment, the conducting element is made fully or partly of at least one cermet, as mentioned above. In addition, one or more other electrical conductors, for example metallic conductors, can be provided. The conducting element can, for example, be provided in the form of one or more contact pins and/or curved conductors. Moreover, the conducting element can include, for example, on a side of the base body and/or electrical bushing facing the internal space or on a side of the base body and/or electrical bushing facing the external space or accessible from the external space, one or more connecting contacts, for example one or more plug-in connectors, for example one or more connecting contacts, which project from the base body or can be electrically contacted through other means from the internal space and/or the external space.

The at least one conducting element can establish the electrically conducting connection between the internal space and the external space in a variety of ways. For example, the conducting element can extend from at least one section of the conducting element that is arranged on the side of the base body facing the internal space to at least one section of the conducting element arranged on the side facing the external space or accessible from the external space. However, other arrangements are also feasible as a matter of principle. Accordingly, the conducting element can just as well include a plurality of partial conducting elements that are connected to each other in an electrically conducting manner. Moreover, the conducting element can extend into the internal space and/or the external space. For example, the conducting element can include at least one region that is arranged in the internal space and/or at least one region that is arranged in the external space, whereby the regions can, for example, be electrically connected to each other. Various exemplary embodiments shall be illustrated in more detail below.

The at least one conducting element can include, on a side of the base body and/or electrical bushing facing the internal space or on a side of the base body and/or electrical bushing facing the external space or accessible from the external space, at least one electrical connecting element and/or be connected to an electrical connecting element of this type. For example, as described above, one or more plug-in connectors and/or one or more contact surfaces and/or one or more contact springs and/or one or more types of electrical connecting elements can be provided on one or both of said sides. The at least one optional connecting element can, for example, be a component of the at least one conducting element and/or can be connected to the at least one conducting element in an electrically conducting manner. For example, one or more conducting elements of the bushing can be contacted to one or more internal connecting elements and/or one or more external connecting elements. The material of the internal connecting elements should be suited for permanent connection to the conducting element. The external connecting elements should be biocompatible and should be such that they can be permanently connected to the at least one conducting element.

The electrically insulating base body can support, as a bearing, for example, the at least one conducting element. The at least one material of the base body should in one embodiment be biocompatible, as illustrated above, and should have sufficiently high insulation resistance. It has proven to be advantageous in one embodiment for the base body to include one or more materials selected from the group consisting of: aluminum oxide ($Al_2O_3$), zirconium dioxide ($ZrO_2$), aluminum oxide-toughened zirconium oxide (ZTA), zirconium oxide-toughened aluminum oxide (ZTA—Zirconia Toughened Aluminum—$Al_2O_3/ZrO_2$), yttrium-toughened zirconium oxide (Y-TZP), aluminum nitride (AlN), magnesium oxide (MgO), piezoceramic materials, barium (Zr, Ti) oxide, barium (CE, Ti) oxide, and sodium-potassium-niobate. The materials are also called materials and, for example, can be provided as compositions of materials.

An edge body, also called holding element, reaches around the base body and serves as connecting element to the housing of the implantable device. The materials of the edge body must be biocompatible, easy to process, corrosion-resistant, and permanently connectable to the base body and the housing in a firmly bonded manner. It has proven to be advantageous in one embodiment for the edge body to include at least one of the following metals and/or an alloy based on at least one of the following metals: platinum, iridium, niobium, molybdenum, tantalum, tungsten, titanium, cobalt-chromium alloys or zirconium. Alternatively, the edge body can include a cermet, whereby a cermet is also advantageous in one embodiment with regard to tight sealing and manufacturing method.

In the proposed electrical bushing, the at least one conducting element includes at least one cermet.

The base body can, for example, be made fully or partly from one or more sinterable materials, for example, from one or more ceramic-based sinterable materials. The conducting element or elements can fully or partly be made of one or more cermet-based sinterable materials. Moreover, the at least one conducting element can also, as mentioned above, include one or more additional conductors, for example one or more metallic conductors.

In the scope of one embodiment, "cermet" shall refer to a composite material made of one or more ceramic materials in at least one metallic matrix or a composite material made of one or more metallic materials in at least one ceramic matrix. For production of a cermet, for example, a mixture of at least one ceramic powder and at least one metallic powder can be used to which, for example, at least one binding agent and, if applicable, at least one solvent can be added. The ceramic powder or powders of the cermet in one embodiment have a mean grain size of less than 10 µm, in one embodiment less than 5 µm, and in one embodiment less than 3 µm. The metallic powder or powders of the cermet in one embodiment have a mean grain size of less than 15 µm, in one embodiment less than 10 µm, and in one embodiment less than 5 µm. For production of a base body, for example, at least one ceramic powder can be used to which, for example, at least one binding agent and, if applicable, at least one solvent can be added. In this context, the ceramic powder or powders in one embodiment has/have a mean grain size of less than 10 µm (1 µm are equal to $1\times10^{-6}$ m), in one embodiment less than 5 µm, in one embodiment less than 3 µm. For example, the median value or the d50 value of the grain size distribution is considered to be the mean grain size in this context. The d50 value corresponds to the value at which 50 percent of the grains of the ceramic powder and/or metallic powder are finer and 50% are coarser than the d50 value.

In the scope of one embodiment, sintering or a sintering process shall generally be understood to mean a method for producing materials or work-pieces, in which powdered, for example, fine-grained, ceramic and/or metallic substances are heated and thus connected. This process can proceed without applying external pressure onto the substance to be heated or can, for example, proceed under elevated pressure onto the substance to be heated, for example under a pressure of at least 2 bar, in one embodiment higher pressures, for example pressures of at least 10 bar, for example, at least 100 bar, or even at least 1000 bar. The process can proceed, for example, fully, or partly at temperatures below the melting temperature of the powdered material, for example at temperatures of 700° C. to 1400° C. The process can be implemented, for example, fully, or partly in a tool and/or a mould such that a forming step can be associated with the sintering process. Aside from the powdered materials, a starting material for the sintering process can include further materials, for example one or more binding agents and/or one or more solvents. The sintering process can proceed in one or more steps, whereby additional steps can precede the sintering process, for example one or more forming steps and/or one or more debinding steps.

A method can be used, for example, in the manufacture of the at least one conducting element and/or optionally in the manufacture of the at least one base body, in which at least one green compact is manufactured first, subsequently at least one brown compact is manufactured from said green compact, and subsequently the finished work-piece is manufactured from said brown compact through at least one sintering step. In this context, separate green compacts and/or separate brown compacts can be manufactured for the conducting element and the base body and can be connected subsequently. Alternatively, one or more common green compacts and/or brown compacts can be produced for the base body and the conducting element. Alternatively again, separate green compacts can be produced first, said green compacts can then be connected, and subsequently a common brown compact can be produced from the connected green compact. In general, a green compact shall be understood to mean a pre-form body of a work-piece which includes the starting material, for example the at least one ceramic and/or metallic powder, as well as, if applicable, the one or more binding agents and/or one or more solvents. A brown compact shall be understood to mean a pre-form body which is generated from the green compact through at least one debinding step, for example at least one thermal and/or chemical debinding step, whereby the at least one binding agent and/or the at least one solvent is/are removed, at least partly, from the pre-form body in the debinding step.

The sintering process, for example, of a cermet, but of the base body just as well, for example, can proceed comparable to a sintering process that is commonly used for homogeneous powders. For example, the material can be compacted in the sintering process at high temperature and, if applicable, high pressure such that the cermet is virtually sealed tight or has no more than closed porosity. Usually, cermets are characterized by their particularly high toughness and wear resistance. Compared to sintered hard metals, a cermet-containing transmission element usually has a higher thermal shock and oxidation resistance and usually a thermal expansion coefficient that is matched to a surrounding insulator.

For the bushing according to one embodiment, the at least one ceramic component of the cermet can include, for example, at least one of the following materials: aluminum oxide ($Al_2O_3$), zirconium dioxide ($ZrO_2$), aluminum oxide-toughened zirconium oxide (ZTA), zirconium oxide-toughened aluminum oxide (ZTA—Zirconia Toughened Aluminum—$Al_2O_3/ZrO_2$), yttrium-toughened zirconium oxide (Y-TZP), aluminum nitride (AlN), magnesium oxide (MgO), piezoceramic materials, barium (Zr, Ti) oxide, barium (CE, Ti) oxide, or sodium-potassium-niobate.

For the bushing according to one embodiment, the at least one metallic component of the cermet can include, for example, at least one of the following metals and/or an alloy based on at least one of the following metals: platinum, iridium, niobium, molybdenum, tantalum, tungsten, titanium, cobalt or zirconium. An electrically conductive connection is usually established in the cermet when the metal content exceeds the so-called percolation threshold at which the metal particles in the sintered cermet are connected to each other, at least in spots, such that electrical conduction is enabled. For this purpose, experience tells that in one embodiment the metal content should be 25% by volume and more, in one embodiment 32% by volume, in one embodiment more than 38% by volume, depending on the selection of materials.

In the scope of one embodiment, the terms, "including a cermet," "cermet-including," "comprising a cermet," and "cermet-containing", are used synonymously. Accordingly, the terms refer to the property of an element, being that the element contains cermet. This meaning also includes the variant of an embodiment in that elements, for example the conducting element, consist of a cermet, that is, are fully made of a cermet.

In one embodiment, both the at least one conducting element and the base body can include one or more components which are or can be manufactured in a sintering procedure, or the at least one conducting element and the base body are or can both be manufactured in a sintering procedure. For example, the base body and the conducting element are or can be manufactured in a co-sintering procedure, that is, a procedure of simultaneous sintering of these elements. For example, the conducting element and the base body each can include one or more ceramic components that are manufactured, and in one embodiment compacted, in the scope of at least one sintering procedure.

For example, a base body green compact can be manufactured from an insulating composition of materials. This can proceed, for example, by compressing the composition of materials in a mould. In this context, the insulating composition of materials is a powder mass in one embodiment, in which the powder particles show at least minimal cohesion. In this context, the production of a green compact proceeds, for example, through compressing powder masses or through forming by plastic shaping or casting and subsequent drying.

Said procedural steps can also be utilized to form at least one cermet-containing conducting element green compact. In this context, one embodiment can provide that the powder, which is compressed to form the conducting element green compact, is cermet-containing or consists of a cermet or includes at least one starting material for a cermet. Subsequently, the two green compacts—the base body green compact and the conducting element green compact—can be combined. The production of the conducting element green compact and the base body green compact can just as well proceed simultaneously, for example, by multi-component injection molding, co-extrusion, etc., such that there is no longer a need to connect them subsequently.

While the green compacts are being sintered, they are in one embodiment subjected to a heat treatment below the melting temperature of the powder particles of the green compact. This usually leads to compaction of the material and ensuing substantial reduction of the porosity and volume of the green compacts. Accordingly, one particularity of the method is that the base body and the conducting element can in one embodiment be sintered jointly. Accordingly, there is in one embodiment no longer a need to connect the two elements subsequently.

Through the sintering, the conducting element becomes connected to the base body in one embodiment in a positive fit-type and/or non-positive fit-type and/or firmly bonded manner. This in one embodiment achieves hermetic integration of the conducting element into the base body. in one embodiment, there is no longer a need for subsequent soldering or welding of the conducting element into the base body. Rather, a hermetically sealing connection between the base body and the conducting element is attained through the joint sintering in one embodiment and utilization of a cermet-containing green compact in one embodiment.

One refinement of the method is characterized in that the sintering includes only partial sintering of the at least one optional base body green compact, whereby said partial sintering can effect and/or include, for example, the debinding step mentioned above. In one embodiment, the green compact is heat-treated in the scope of said partial sintering. This is usually already associated with some shrinkage of the volume of the green compact. However, the volume of the green compact has not yet reached its final state. Rather, another heat treatment is usually needed—a final sintering—in which the green compact(s) is/are shrunk to its/their final size. In the scope of said variant of an embodiment, the green compact is in one embodiment sintered only partly in order to attain a certain stability to render the green compact easier to handle.

The starting material used for producing at least one conducting element green compact and/or at least one base body green compact can, for example, be a dry powder or include a dry powder, whereby the dry powder is compressed in the dry state into a green compact and shows sufficient adhesion to maintain its compressed green compact shape. However, optionally, the starting material can include one or more further components in addition to the at least one powder, for example, as mentioned above, one or more binding agents and/or one or more solvents. Said binding agents and/or solvents, for example organic and/or inorganic binding agents and/or solvents, are generally known to the person skilled in the art, and are commercially available, for example. The starting material can, for example, include one or more slurries or be a slurry. In the scope of one embodiment, a slurry is a suspension of particles of a powder made of one or more materials in a liquid binding agent, and, if applicable, in a water-based or organic binding agent. A slurry has a high viscosity and can easily be formed into a green compact without the application of high pressure, for example through casting or injection molding or plastic forming.

In the case of green compacts made from slurries, the sintering process, which is generally carried out below the melting temperature of the ceramic, cermet or metal materials that are used, but in individual cases can also be carried out just above the melting temperature of the lower melting component of a multi-component mixture, this usually being the metal component, leads to the binding agent slowly diffusing from the slurry. Overly rapid heating leads to a rapid increase of the volume of the binding agent by transition to the gas phase and destruction of the green compact or formation of undesired defects in the work-piece.

Thermoplastic and duroplastic polymers, waxes, thermogelling substances and/or surface-active substances, for example, can be used as binding agent—also called binder. In this context, these can be used alone or as binding agent mixtures of multiple components of this type. If individual elements or all elements of the bushing (base body green compact, conducting element green compact, bushing blank) are produced in the scope of an extrusion procedure, the composition of the binding agent should be such that the line of the elements extruded through the nozzle is sufficiently stable in shape for the shape defined by the nozzle to easily be maintained. Suitable binders, also called binding agents, are known to the person skilled in the art.

In contrast to one embodiment, according to which a conducting element includes at least one cermet, the prior art has a metallic wire or other metallic work-piece be the conducting element. A conducting element, which, according to one embodiment, is provided with a cermet, can be connected to the base body easily, since the cermet and the insulation element are or include ceramic substances and/or a ceramic material. The base body can also be called insulation element in order to address the electrical function; in this context, the two terms are exchangeable. Green compacts of both the conducting element and the base body can be produced and subsequently subjected to a sintering process. The resulting electrical bushing is not only particularly biocompatible and durable, but also possesses good hermetic sealing properties. Thus, no fissures or connecting sites still to be soldered result between the conducting element and the base body. Rather, sintering results in the base body and the conducting element becoming connected. A variant of an embodiment therefore provides the at least one conducting element to consist of a cermet. In this variant of an embodiment, the conducting element includes not only components made of cermet, but is fully made of a cermet.

Generally, cermets are characterized by their particularly high toughness and wear resistance. The "cermets" and/or "cermet-containing" substances can, for example, be or include cutting materials related to hard metals which can dispense with tungsten carbide as the hard substance and can be produced, for example, by a powder metallurgical route. A sintering process for cermets and/or the cermet-containing conducting element proceeds, for example, alike a process for homogeneous powders except that, at identical compression force, the metal is usually compacted more strongly than the ceramic material. Compared to sintered hard metals, the cermet-containing conducting element usually shows higher resistance to thermal shock and oxidation. As mentioned above, the ceramic components can be, for example, aluminum oxide ($Al_2O_3$) and/or zirconium dioxide ($ZrO_2$), whereas for example, niobium, molybdenum, titanium, cobalt, zirconium, chromium are conceivable as metallic components.

For integration of the electrical bushing into the housing of a cardiac pacemaker, the electrical bushing can include a holding element. Said holding element is arranged about the base body in a wreath-like arrangement. The term, wreath-like, is used to refer to a sleeve shape with a rim that extends radially outward. The holding element surrounds the base body, in one embodiment along its entire circumference. The purpose of the holding element is to establish a non-positive fit- and/or positive fit-type connection to the housing. A fluid-tight connection between the holding element and the housing must be established in the process. In one embodiment, the electrical bushing includes a holding element that includes a cermet. The cermet-containing holding element can be connected to the housing of the implantable medical device in an easy, durable and hermetically sealed manner. Another embodiment provides the holding element to not only include a cermet, but to consist of a cermet. Moreover, it is conceivable that the conducting element and the holding element are made from the same material. In this variant, the same materials are used for both the conducting element and the holding element. This relates, for example, to a durable, conductive, and biocompatible cermet. Since both the holding element and the conducting element are still to be connected to metallic components, both must include means to be welded or soldered to them. If a cermet is found that meets the pre-requisites specified above, said cermet can be used for both the holding element and the conducting element in order to obtain a particularly inexpensive electrical bushing.

In electrical terms, the base body can also be considered to be an insulation element that is electrically insulating. The base body is made from an electrically insulating material, in one embodiment from an electrically insulating composition of materials. The base body is set up to electrically insulate the conducting element from the holding element or—(in case no holding element is provided)—from the housing and/or other objects of the implantable medical device. Electrical signals that are propagated through the conducting wire shall not be attenuated or short-circuited by contacting the housing of the implantable device. In addition, the composition of the base body must be biocompatible for implantation in medical applications. For this reason, it is preferred in one embodiment that the base body consists of a glass-ceramic or glass-like material. It has been found to be preferred in one embodiment that the insulating composition of materials of the base body is at least any one from the group, aluminum oxide ($Al_2O_3$), magnesium oxide (MgO), zirconium oxide ($ZrO_2$), aluminum titanate ($Al_2TiO_5$), and piezoceramic materials. In this context, aluminum oxide features high electrical resistance and low dielectric losses. These properties are supplemented by the additional high thermal resistance and good biocompatibility.

Another refinement of the bushing according to one embodiment is characterized in that the holding element includes at least one flange, whereby the flange, for example, is conductive like a metal. The purpose of the flange is to seal the electrical bushing with respect to a housing of the implantable device. The holding element holds the electrical bushing in the implantable device. In the variant of an embodiment described herein, the holding element includes at least one flange on an external side. These flanges form a bearing, which can be engaged by the lids of the implantable medical device, in particularly engaged in a tightly sealing manner. Accordingly, the holding element including the flanges connected to it can have a U- or H-shaped cross-section. Integrating at least one flange into the holding element ensures that the electrical bushing is integrated into the implantable device in a safe, impact-resistant and durable manner. In addition, the flanges can be provided such that the lids of the implantable device are connected clip-like to the holding element in a non-positive fit-type or positive fit-type manner.

Another refinement of the electrical bushing according to one embodiment is characterized in that the at least one flange includes a cermet. In the scope of said variant of an embodiment, both the holding element and the flange include a cermet. In one embodiment, both the flange and the holding element are made of the same material. By providing the flange as a cermet, the flange can be sintered easily and inexpensively as part of the holding element jointly with the insulation element and the conducting element in the scope of the method to be described below.

One embodiment also includes a use of at least one cermet-including conducting element in an electrical bushing for an implantable medical device. Features and details that were described in the context of the electrical bushing and/or the method shall obviously also apply in relation to the use of a cermet-containing conducting element.

The scope of one embodiment also includes an implantable medical device, for example, a cardiac pacemaker or defibrillator, having an electrical bushing according to at least one of the preceding claims. Features and details that were described in the context of the electrical bushing and/or the method shall obviously also apply in relation to the implantable medical device.

Features and properties that are described in the context of the electrical bushing shall also apply in relation to the method according to one embodiment, and vice versa.

The method according to one embodiment provides both the base body and the conducting element to include ceramic components that are processed in the scope of a sintering process. In the scope of step a), a base body green compact is generated from an insulating composition of materials. This can be done by compressing the composition of materials in a mould. In this context, the insulating composition of materials advantageously in one embodiment is a powder mass, in which the powder particles at least minimal cohesion. Usually, this is effected in that a grain size of the powder particles does not exceed 0.5 mm. In one embodiment, the mean grain size is no larger than 10 p.m. In this context, the manufacture of the green compact proceeds either by compressing powder masses or by forming and subsequent drying. Said procedural steps are also utilized to form the cermet-containing conducting element green compact. In this context, one embodiment provides the powder, which is compressed into the conducting element green compact, to be cermet-containing or to consist of a cermet. The green compacts—for example, the base body green compact and the conducting element green compact—are one embodiment combined subsequent to this step. After this step, which is called step c), the two green compacts are subjected to firing—which is also called sintering. In the process of sintering or firing, the green compacts are subjected to a heat treatment below the melting temperature of the powder particles of the green compact. This leads to a substantial reduction of the porosity and volume of the green compacts. The special feature according to one embodiment of the method is therefore that the base body and the conducting element are jointly subjected to firing and the conducting element is generated to have at least one conductive surface. Subsequently, there is no longer a need to connect the two elements and, for example, there is no need to generate a conductive surface in an additional step. Through the firing process, the conducting element becomes connected to the base body in a positive fit-type and/or non-positive fit-type and/or firmly bonded manner. This achieves hermetic integration of the conducting element into the base body. There is no longer a need for subsequent soldering or welding of the conducting element into the base body. Rather, through the joint firing and the utilization of a cermet-containing green compact, that is, of the conducting element green compact, a hermetically sealing connection between the base body and the conducting element is attained.

One refinement of the method according to one embodiment is characterized in that step a) includes a partial sintering of the base body green compact. The green compact of the insulation element is heat-treated in the scope of said partial sintering. This is already associated with some shrinkage of the volume of the insulation element green compact. However, the volume of the green compact does not reach its final state. Rather, this requires another heat treatment in the scope of step d), in which the base body green compact with the conducting element green compact are shrunk to their final size. In the scope of said variant of an embodiment, the green compact is heat treated only partly in order to already attain a certain surface hardness to render the base body green compact easier to handle. This is expedient for example, in the case of insulating compositions of materials which can be compressed into a green compact shape only with some difficulty.

For example, a component of the bushing according to one embodiment is called green compact unless all sintering steps have been carried out. Accordingly, even a pre-sintered or partly sintered or heat-treated green compact is called green compact until all heat treatment or sintering steps have been completed.

Another variant of the embodiment is characterized in that the conducting element green compact is also already partly sintered in step b). As described above for the base body green compact, the conducting element green compact can also be partly sintered in order to already attain a certain surface stability. It needs to be noted in this context that the final complete sintering occurs no earlier than in step d). Accordingly, the conducting element green compact attains its final size only in step d).

Another refinement of the method is characterized in that at least one cermet-containing holding element green compact for a holding element is generated. The conducting element green compact is introduced into the base body green compact. The base body green compact is introduced into the holding element green compact. The base body green compact is subjected to firing jointly with the at least one conducting element green compact and the holding element green compact. This results in a base body with a conducting element and a holding element.

The special feature of this procedural step is that, not only the conducting element green compact and the base body green compact, but also the holding element green compact is sintered in one step. All three green compacts are generated, then joined, and subsequently subjected to firing or sintering as a unit. In a particular variant of an embodiment, producing the at least one cermet-containing holding element green compact can include a partial sintering. As before, one embodiment provides the fringe green compact to be partly sintered in order to attain higher surface stability. In this context, the base body green compact can thus form the dielectric layer or a piezoelectric body for the filter structure or a receptacle for a frequency-selective component.

A specific exemplary embodiment of a method for the manufacture of a bushing according to one embodiment is presented in the following.

In the first step, a cermet mass is produced from platinum (Pt) and aluminum oxide ($Al_2O_3$) containing 10% zirconium dioxide ($ZrO_2$). The following starting materials are used for this purpose:

40 vol. % Pt powder with a mean grain size of 10 μm, and
60 vol. % $Al_2O_3/ZrO_2$ powder with a relative $ZrO_2$ content of 10% and a mean grain size of 1 μm.

The two components were mixed, water and a binding agent were added, and the sample was homogenized through a kneading process. Analogous to the first step, a ceramic mass is produced in a second step from a powder with an $Al_2O_3$ content of 90% and a $ZrO_2$ content of 10%. The mean grain size was approx. 1 μm. As before, water and a binding agent were added to the ceramic powder and the sample was homogenized. In a third step, the ceramic mass made of aluminum oxide with a 10% zirconium dioxide content produced in step two was converted to a shape of a base body. Made from the cermet mass produced in the first step, a cermet body that contained a mixture of platinum powder and aluminum oxide with a zirconium dioxide content of 10%, was introduced as green compact into an opening in the base body green compact. Subsequently, the ceramic mass was compacted in the mould. Then the cermet and the ceramic component were subjected to debinding at 500° C. and the sintering was finished at 1650° C.

FIG. 1 illustrates an embodiment of the electrical bushing according to one embodiment with multiple capacitors provided according to one embodiment. The filter structures illustrated in FIG. 1 each include a capacitor, whereby the electrically conductive surface provided according to one embodiment is provided as electrode surface of the respective capacitor.

The electrical bushing 10 illustrated in FIG. 1 is radially surrounded by an optional holding element 20 that is indicated by dashed lines. The optional holding element 20 is made from a conductive material, for example, from a cermet, and includes a circumferential rim in order to simplify the insertion into a housing (not illustrated). Alternatively, the holding element 20 can just as well be provided to be made from metal or a metal alloy.

The electrical bushing 10 includes a conducting element 30 and a base body 40, whereby the base body is electrically insulating and the conducting element is electrically conductive. The bushing illustrated in FIG. 1 includes multiple variants of an electrical filter structure 50a-c that can be used alone or in combination with each other. The conducting element 30 extends fully through the base body 40 and thus provides an electrically conductive connection between an internal space and an external space. In FIG. 1 and in FIGS. 2 and 3 as well, the external space is arranged above the electrical bushing 10 and the internal space is arranged below the electrical bushing 10. In one embodiment, the internal space and/or external space are directly adjacent to the bushing illustrated in the figures.

The filter structure 50a extends from an underside of the electrical bushing that faces the internal space to the upper side of the bushing illustrated that faces the external space. Front surfaces of the conducting element 30 border directly on the space that is adjacent to the upper side and/or the underside of the bushing. The front surfaces of the conducting element 30 can be flush with the upper side and the underside of the bushing as illustrated in FIG. 1, or can be offset towards the inside of the bushing or project from the upper side and/or underside.

The filter structure 50a includes multiple electrically conductive surfaces of which only one is identified by reference number 52a for reasons of clarity. The electrically conductive surfaces form electrode surfaces 52a of a capacitor that is provided by the filter structure 50a. The electrically conductive surfaces are part of the conducting element 30 and thus are connected physically and, for example, electrically to the section of the conducting element 30 that extends from the upper side to the underside of the electrical bushing. The electrode surfaces 52a are plane-parallel to each other and, for example, parallel to the underside and/or upper side of the electrical bushing, and also extend perpendicular to a longitudinal axis of the bushing. Corresponding electrode surfaces 56a are situated opposite from the electrode surfaces 52a and are electrically connected to a connecting section 54a. The connecting section 54a of the conducting element 30 includes a front surface that is provided on the underside of the electrical bushing 10. The front side is provided for example, in order to be electrically connected to a housing or mass. The electrode surfaces 52a and 56a interdigitate. Dielectric layers belonging to the insulating base body 40 are formed each between the electrodes 56a that are connected to the connecting section 54a and the electrodes 52a that are connected to the section of the conducting element 30 that extends through the bushing 10. The filter structure 50a borders on the underside of the electrical bushing 10 that faces the internal space. Alternative embodiments provide for the filter structure, like the one identified through reference number 50a, to be situated on the inside of the electrical bushing or on the upper side.

Reference number 50b denotes a filter structure that borders on the upper side of the electrical bushing 10 which faces the external space. Like filter structure 50a, filter structure 50b also includes electrode surfaces 52b that are connected to a section of the conducting element 30 that extends from the underside to the upper side of the electrical bushing 10. The electrode surfaces 52b extend perpendicular to the direction of extension of the section of the conducting element 30 that extends from the underside to the upper side. Furthermore, the filter structure 50b includes opposite electrode surfaces 56b that are connected to the connecting section 54b. The connecting section 54b includes a front side that borders on the upper side of the electrical bushing.

The filter structures 50a and 50b each include electrode surfaces 52a, b and 56a, b, which form a perpendicular line with respect to the upper side and/or the underside of the electrical bushing. Moreover, the longitudinal axis extends along the section of the conducting element 30 that connects the underside to the upper side. Electrodes 52a, b and 56a, b can extend parallel to the longitudinal axis in an alternative embodiment (not illustrated), whereby the individual electrode surfaces are next to each other in a row in radial direction and are connected alternately to the connecting section, cf. reference number 54b, and to the section of the conducting element 30 that extends from the underside to the upper side. In the latter case, the connecting section has the same electrical function as the connecting section 54a, b of FIG. 1. However, the connecting section of electrodes 52a, b, 56a, b, which extend along the longitudinal axis of the bushing, extend perpendicular with respect to the longitudinal axis. A connecting section having said extension is identified by reference number 54c in FIG. 1.

The electrical bushing illustrated in FIG. 1 further includes a filter structure 50c that borders neither on the underside nor on the upper side of the bushing. The filter structure 50c includes an electrode surface 52c that is provided directly by the section of the conducting element 30 that extends from the underside to the upper side of the bushing 10. The electrode surface 52c is formed by a circumferential surface section of the section of the conducting element 30 that extends from the underside to the upper side of the electrical bushing. An electrode surface 56c that is connected to a connecting section 54c is situated opposite from the electrode surface 52c. The connecting section 54c extends from the electrode 56c to a circumferential surface of the base body 40. At the circumferential surface of the base body 40, the connecting section 54c forms a front surface and/or a contact that can be electrically contacted by a housing or holding element 20 that is situated there. The filter structure 50c illustrated in FIG. 1 includes just one pair of electrode surfaces 52c, 56c.

In an embodiment having multiple electrode surfaces per pole that is not illustrated here, such as are evident, for example, in filter structures 50a and b, the filter structure includes two connecting sections. A first connecting section connects a first group of electrode surfaces to each other and forms a bushing towards the outside, as illustrated by connecting sections 54a-c. A second connecting section connects a second group of electrode surfaces to each other and connects them also directly to the section of the connecting element 30 that extends from the underside to the upper side. The connecting sections are provided as cermet, but can just as well be provided as wires made, for example, of metal or a metal alloy. In one embodiment, the connecting sections are not part of the connecting element provided they are not provided to be made of cermet. Likewise, a subgroup of all electrode surfaces can be provided to be made of a metal alloy or a metal, for example in the form of a metallization layer or a metal or metal alloy foil. Said subgroups of electrode surfaces are not part of the connecting element provided they are not provided to be made of cermet.

In the exemplary embodiment of FIG. 1, the electrically conductive surfaces are electrode surfaces of a capacitor. Alternatively, they can be electrode surfaces of an electromechanical resonator whose piezoelectric body is provided by a section of the base body 40. In the latter case, the electrode surfaces are provided, for example, on the upper side or underside of the electrical bushing.

The variants of an electrical filter structure 50a-c illustrated in FIG. 1 can be used alone or in combination with each other, as has been mentioned above. An electrical bushing according to one embodiment can include, for example, just one of the electrical filter structures 50a-c. Alternatively, a bushing can include the filter structures 50a and 50b or the filter structures 50a and 50c or the filter structures 50b and 50c or the filter structures 50a, 50b, and 50c.

Figure 2:
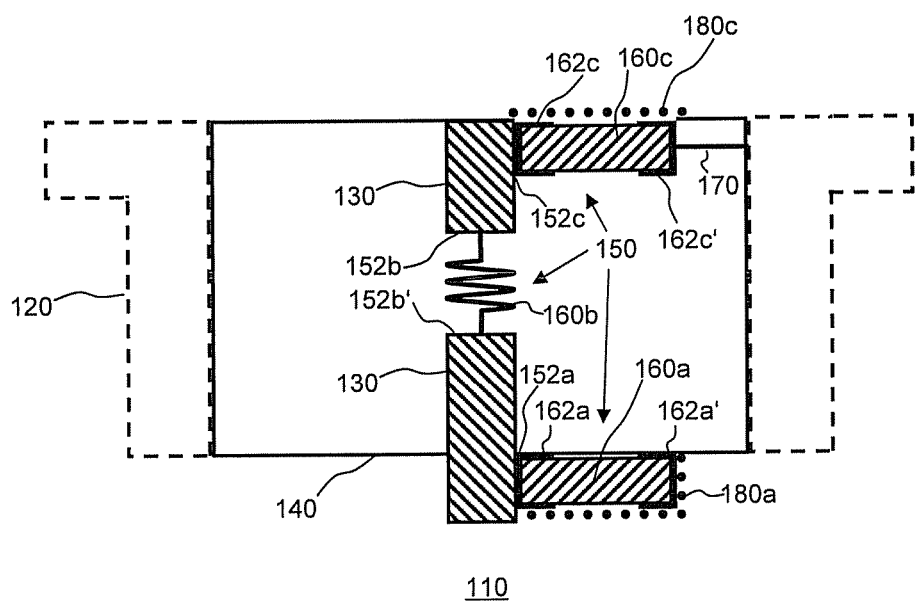
FIG. 2 illustrates a second embodiment of the bushing with multiple variants of filter structures.

FIG. 2 illustrates a second embodiment of the electrical bushing according to one embodiment, whereby the electrode surfaces are provided as contact surfaces for further components. FIG. 2 illustrates multiple variants of contact surfaces and associated arrangement of components. The bushing 110 of FIG. 2 is surrounded by an optional holding element 120 that is illustrated by dashing like in FIG. 1. The bushing 110 further includes a conducting element 130 having a conducting section that extends between the upper side and the underside of the bushing illustrated. Like in FIG. 1, the upper side faces an external space while the underside faces an internal space. The electrical bushing illustrated in FIG. 2 further includes a base body 140, in which the conducting element 130 extends.

According to a variant of the arrangement of contact surfaces and component, the section of the conducting element 130 that extends from the underside to the upper side of the bushing 110 is interrupted and forms at the interruption site a contact surface each that corresponds to the front side of the corresponding section. The contact surfaces are identified by reference numbers 152*b* and 152*b*'. The contact surfaces 152*b* and 152*b*' provided on the internal front surfaces of the conducting element 130 are connected to a component 160*b* that is provided as an inductor in FIG. 2. The component 160*b* includes a coil that is illustrated schematically in FIG. 2. The direction of winding of the coil is essentially perpendicular to the longitudinal axis of the electrical bushing 110. The winding of the component 160*b* can be provided with or without core. The core includes a material having a high relative magnetic permeability.

Another variant of the arrangement of contact surfaces is identified by reference number 152*a*, whereby reference number 152*a* is a contact surface. In this variant, the contact surface is formed by the circumferential surface section of a section of the conducting element 130. The contact surface 152*a* is situated on a section of the conducting element that projects from the base body 140. Moreover, according to said variant, a capacitor 160*a* that is provided as an SMD component includes a connection surface 162*a* that is electrically connected to the contact surface 152*a*, for example through a solder connection. A second connection surface 162' of the capacitor 160*a* is provided for connection, for example, to the holding element 120 or any other electrical potential. Since the capacitor 160*a* is attached on the base body, component 160*a* is fully covered by a protective layer 180*a*. The protective layer is optional and only indicated schematically through a dashed line.

Moreover, FIG. 2 illustrates a variant, in which the filter structure 150 includes, aside from the capacitor 160*a* and the inductor 160*b*, another capacitor 160*c* that is arranged in a recess of the base body 140. A circumferential surface section of a section of the conducting element 160 forms a contact surface 152*c* that is connected to a connection surface 162*c* of the capacitor 160*c*. Another connection surface 162*c*' of the capacitor 160*c* is connected to an external circumferential surface of the base body 140 through a connecting section 170. The connecting section 170 forms on the external circumferential surface of the base body 140 a front side that serves as contact surface. Accordingly, an adjacent holding element 120, for example, that is provided to be electrically conductive is thus electrically connected to the connecting section 170 and thus to the connection surface 162*c*' of the capacitor 160*c*.

While the electrical component 160*a* is arranged on the base body 140, the component 160*c* is situated in a recess or niche that is provided in a surface of the base body 140. Accordingly, the component 160*c* is embedded into the base body 140 of the electrical bushing 110. Like component 160*a*, component 160*c* also is covered by a protective layer 180*c* that is only indicated schematically through a dashed line.

The variants illustrated in FIG. 2 can be combined at will. A bushing according to one embodiment can include one or more of the variants illustrated in FIG. 2. A bushing according to one embodiment can, for example, include one, more or all variants of contact surfaces 152*a*-152*c*' and can likewise include one, more or all components 160*a*-*c*. The components 160*a*-*c* can each be connected to the remaining conducting element section through any variant of the contact surface; for example a component 160 *b* can be connected to the contact surfaces 152*a*,*c* (that is, be embedded into the base element or not). Moreover, a component 160*a* or *c* can be connected in the same manner as illustrated through reference numbers 152 *b*, *b*'. In a specific embodiment, the contact surfaces 162*a*' or *c*' are connected to conducting element sections, for example in order to form an LC anti-resonant circuit together with the inductor 160*b*. Moreover, a side surface of the conducting element, one embodiment situated within the base body, can form a contact surface for a frequency-selective component, for example, for a capacitor with an independent body. Being an in-series dissipation filter, said capacitor is also connected to mass or a different potential, one embodiment through a contact surface made of a cermet.

The variants of an electrical filter structure 50*a*-*c* can be used alone or in combination, as has been mentioned above. An electrical bushing according to one embodiment can include, for example, just one of the electrical filter structures 50*a*-*c*. Alternatively, a bushing can include the filter structures 50*a* and 50*b* or the filter structures 50*a* and 50*c* or the filter structures 50*b* and 50*c* or the filter structures 50*a*, 50*b*, and 50*c*.

The filter structure 150 illustrated in FIG. 2 forms a continuity filter in a π-arrangement of two parallel capacitors 160*a*, *c* and one serial inductor 160*b* arranged in between. Alternatively to the embodiment illustrated in FIG. 2, at least one of the capacitors 160*a* or 160*c* can be provided through electrode surfaces that are provided by the conducting element. For example, one of the capacitors can be provided as illustrated in FIG. 1.

Figure 3:
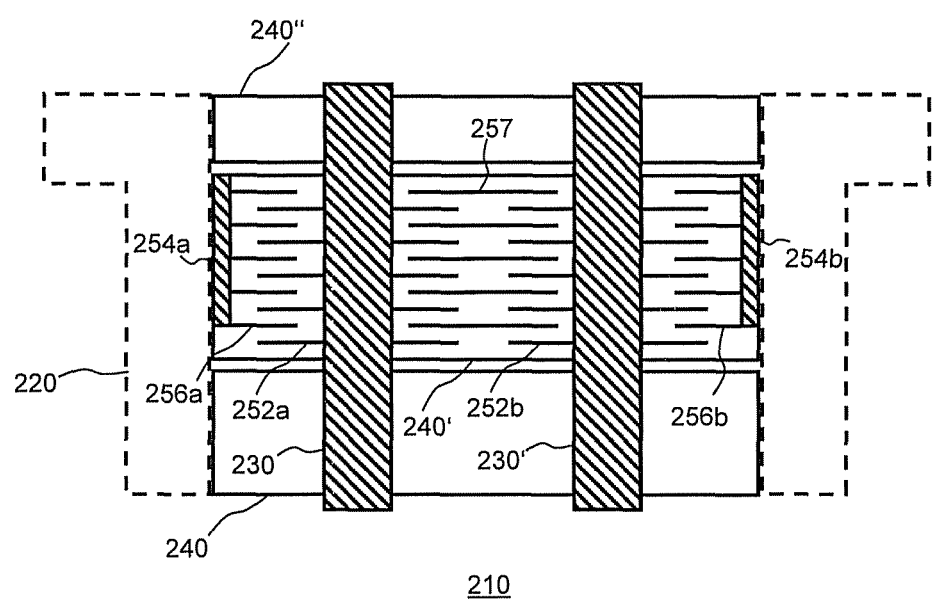
FIG. 3 illustrates a third embodiment of the bushing with multiple possible arrangements of filter structures.

FIG. 3 illustrates a third embodiment of the electrical bushing according to one embodiment. The electrical bushing 210 illustrated in FIG. 3 is surrounded by an optional holding element 220 that is indicated by dashing. Bushing 210 includes two conducting elements 230, 230' that extend through a base body. The base body consists of multiple parts, for example, three parts, in the embodiment illustrated in FIG. 3. Accordingly, the base body includes the base body sections 240, 240', and 240". While the base body sections 240 and 240" include no filter structure, the base body section 240' situated in between provides a capacitive filter arrangement. For this purpose, the conducting elements 230, 230' form electrically conductive surfaces 252*a*, 252*b*, which are provided as electrode surfaces. The conducting element 230 further forms opposite electrode surfaces 256*a*, *b*. The electrode surfaces 256*a* and *b* each are connected to each other through an associated connecting element 254*a*. The connecting elements 254*a*, *b* include a rear side that is provided on an external circumferential surface of the section 240' of the base body. This enables direct electrical contact, for example to the adjacent holding element 220. Further electrode surfaces 257 are provided by cermet and are situated in the section 240' of the base body. These are one embodiment electrically connected to the electrode surfaces 256*a* and 256*b*. The electrodes 256*a*, 256*b*, and 257 can be provided to be continuous and include cut-outs through which the sections of the conducting elements 230, 230' extend, which connect the upper side of the section 240" to the underside of the section 240 of the base body. In this context, the underside of the electrical bushing 210 faces the internal space, whereas the upper side of the bushing 210 faces the external space.

Electrical connections between said components and further components of the bushing or components to be fastened to the bushing (the holding element, for example) are provided, for example, through solder connections, though direct contacting, for example by means of a press fit, or through electrically conductive adhesives and/or in general through a firmly bonded electrically conductive connection. Furthermore, the electrically conductive firmly bonded connection can be provided by providing, for example, the cermet as a single part.

The sections 240-240" illustrated in FIG. 3 are illustrated as separate bodies for reasons of clarity. In one embodiment, there is no gap between these sections of the base body, whereby the sections are connected to each other in a firmly bonded manner, for example, by providing the base body as a single part. If the sections 240-240" of the base body are separate individual bodies, though, as illustrated in FIG. 3, said bodies can be connected to each other consecutively, for example, through firmly bonding connection techniques. Sintering, for example, is one such firmly bonding connection technique, whereby other such connection techniques, such as gluing or soldering, are feasible just as well. Moreover, the holding element 220 can connect the sections 240-240" to each other. This applies to all sections 240-240" or just to sub-groups of sections 240, 240', and 240". The embodiment illustrated in FIG. 3 can, for example, be combined with individual variants or embodiments of FIGS. 1 and 2.

Figure 4:
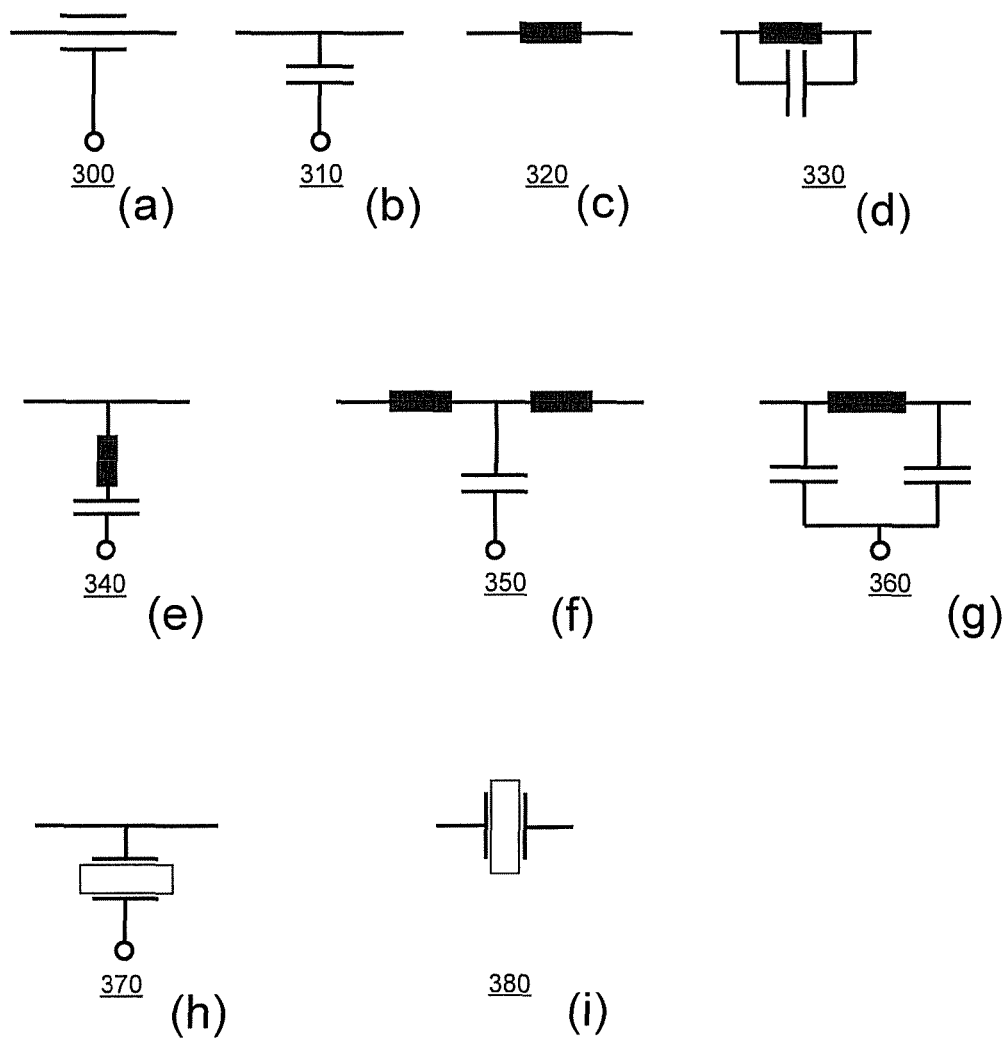
FIGS. 4(a)-(i) illustrate exemplary circuiting schemes that form the filter structure of the electrical bushing.

FIGS. 4(a)-(i) illustrate multiple variants of circuits that can be provided by the filter structure of the bushing according to one embodiment. The variants of circuits can represent the entire filter structure or just a part thereof. For example, several of the variants of circuits illustrated in FIGS. 4(a)-(i) can be combined with each other in a bushing, for example, by serial combination of feedthrough filter circuits and/or parallel combination of dissipation filter circuits. The upper, horizontal branch of the variants of circuits illustrated in FIGS. 4(a)-(i) corresponds to the section of the conducting element that extends through the base body and/or the electrically conductive connection. The connector illustrated as a circle corresponds to a bonding to mass, for example to a connector that is connected to the housing or to a holding element. FIG. 4(a) illustrates a capacitive feedthrough filter, in which HF portions are deviated to mass, whereby the electrically conductive connection is coupled in a capacitive manner. FIG. 4(b) illustrates a parallel dissipation filter, in which HF portions are also deviated to mass, whereby the capacitor is connected to the feedthrough. FIG. 4(c) illustrates a serial filter inductor in the electrically conductive connection that blocks HF portions and allows only low frequency portions to pass. FIG. 4(d) illustrates an LC anti-resonant circuit that is connected in-series to the electrically conductive connection between the internal space and the external space. It forms a barrier for portions with a frequency near the resonance frequency and blocks said portions. FIG. 4(e) illustrates an LC resonant circuit that is connected as dissipation filter to the electrically conductive connection between the internal space and the external space. It forms a barrier for portions with a frequency near the resonance frequency and dissipates said parts to mass. FIG. 4(f) illustrates a continuity filter in a T-arrangement with two serial inductors and a parallel capacitor arranged in between. The parallel capacitor is connected to a tapping between the two serial inductors and to mass. This results in a second order low-pass filter. FIG. 4(g) illustrates a continuity filter in a π-arrangement with two parallel capacitors and a serial inductor arranged in between. The serial inductor connects the capacitors, which are in a parallel arrangement, to each other, whereby the parallel capacitors each are connected between the electrically conductive connection of the conducting element and mass. This results in a second order low-pass filter. Alternatives to the variants or circuits illustrated in FIGS. 4(f) and 4(g) each use a parallel circuit including an inductor and a capacitor instead of the inductors, and a serial circuit including an inductor and a capacitor each instead of the capacitors. This results in higher order band-stop filters. FIG. 4(h) illustrates an electromechanical dissipation filter, whereby a crystal oscillator, SAW filter or BAW filter is used as frequency-selective component. Undesired frequency portions are diverted to mass, that is, to the housing. FIG. 4(i) illustrates an electromechanical serial filter, whereby a crystal oscillator, SAW filter or BAW filter is used as frequency-selective component. Undesired frequency portions are not transmitted and/or are blocked.

The filter structure in one embodiment provides a low-pass filter or a band-stop filter providing strong attenuation of HF frequencies that are used for excitation in medical magnetic resonance imaging procedures for whole body imaging. Said HF frequencies are, for example, between 1 and 1000 MHz, for example in the ultra-short wave range from 30 to 300 MHz and/or in one embodiment at approx. B*42 MHz/Tesla, whereby B is the magnetic flux density of the static magnetic field used for magnetic resonance imaging. The value of B is assumed to be between 0.2 and 5 Tesla, in one embodiment from 1-2 Tesla. Alternatively, the value of B can be assumed to be 5-12 Tesla for modern and/or future MRI systems.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of the specific embodiments discussed herein. Therefore, it is intended that this invention be limited only by the claims and the equivalents thereof.

What is claimed is:

1. An electrical bushing for use in a housing of an implantable medical device, whereby the electrical bushing comprises at least one electrically insulating base body and at least one electrical conducting element;

whereby the conducting element establishes, though the base body, at least one electrically conductive connection between an internal space of the housing and an external space;

whereby the conducting element is hermetically sealed with respect to the base body; and characterized in that the electrical bushing comprises an electrical filter structure, whereby the at least one conducting element provides at least one electrically conductive surface of the filter structure and such that the conducting element and the electrically conductive surface of the filter structure both comprise at least one cermet such that they are connected through a firmly bonded, electrically conductive connection and are part of the same structure and such that there is no connective material or gaps therebetween.

2. The electrical bushing according to claim 1, whereby the filter structure comprises a capacitor or an electromechanical resonator and the at least one electrically conductive surface of the filter structure provides at least one electrode surface of the capacitor or of the electromechanical resonator.

3. The electrical bushing according to claim 2, whereby a section of the electrically insulating base body provides a dielectric layer of the capacitor or a piezoelectric body of the electromechanical resonator.

4. The electrical bushing according to claim 2, whereby the at least one electrically conductive surface of the filter structure provides multiple electrode surfaces of the capacitor that extend plane parallel to each other, whereby the conducting element further comprises at least one connecting section that extends from one of the electrode surfaces to at least one other of the electrode surfaces in order to connect them electrically.

5. The electrical bushing according to claim 1, whereby the filter structure comprises a frequency-selective component and the at least one electrically conductive surface of the filter structure provides at least one contact surface to which the component is connected, whereby the frequency-selective component is provided as capacitor, as inductor, as electromechanical resonator, as SAW filter, as BAW filter, as crystal oscillator or as an integrated filter circuit.

6. The electrical bushing according to claim 5, whereby the frequency-selective component comprises at least one connector that is physically connected to the contact surface through a solder connection or through a press-fit.

7. The electrical bushing according to claim 1, whereby the at least one electrically conductive surface extends parallel or perpendicular to a direction of longitudinal extension of the base body and the at least one electrically conductive surface is essentially planar, convex, circular cylinder-shaped or extends along a section of a circular cylinder or sphere.

8. The electrical bushing according to claim 1, whereby the bushing comprises multiple conducting elements which each provide a conductive surface of the filter structure.

9. The electrical bushing according to claim 1, whereby at least one of the filter structure and the at least one electrically conductive surface is arranged at a surface of the bushing that is provided to border on the internal space or on the external space.

10. The electrical bushing according to claim 1, whereby the filter structure provides a band-stop filter or a low-pass filter and the filter structure comprises a capacitive feedthrough filter, a parallel dissipation capacitor, a serial filter inductor, an LC anti-resonant circuit that is arranged in series with the electrically conductive connection between the internal space and the external space, an LC resonant circuit that is connected as dissipation filter to the electrically conductive connection between the internal space and the external space, a continuity filter in a T arrangement of two serial inductors and a parallel capacitor in between, a continuity filter in a it arrangement of two parallel capacitors and a serial inductor in between, an electromechanical dissipation filter or an electromechanical serial filter.

11. The electrical bushing according to claim 1, whereby the base body and the at least one conducting element are connected in a firmly bonded sintered connection.

12. The electrical bushing according to claim 1, whereby at least one of the filter structure and the at least one electrically conductive surface is arranged within the bushing.

13. The electrical bushing according to claim 1, whereby the filter structure comprises a first connecting section connecting a first group of electrode surfaces to each other and to the internal space of the housing and a second connecting section connecting a second group of electrode surfaces to each other and to the external space of the housing.

14. An implantable medical device comprising:
a housing; and
an electrical bushing used in the housing;
whereby the electrical bushing comprises at least one electrically insulating base body and at least one electrical conducting element;
whereby the conducting element establishes, though the base body, at least one electrically conductive connection between an internal space of the housing and an external space;
whereby the conducting element is hermetically sealed with respect to the base body; and
characterized in that the electrical bushing comprises an electrical filter structure, whereby the at least one conducting element provides at least one electrically conductive surface of the filter structure and such that the conducting element and the electrically conductive surface of the filter structure comprise at least one cermet such that they are connected through a firmly bonded, electrically conductive connection and in that there is no solder, braze or conductive thermal material and no gaps between the electrical filter structure and the conducting element.

15. The implantable medical device according to claim 14, whereby device comprises a cardiac pacemaker or defibrillator.

* * * * *